United States Patent [19]
Koch et al.

[11] Patent Number: 5,882,851
[45] Date of Patent: Mar. 16, 1999

[54] CYTOCHROME P-450 MONOOXYGENASES

[75] Inventors: Birgit Maria Koch, Vanløse; Ole Sibbesen, Roskilde; Barbara Ann Halkier, Copenhagen V; Birger Lindberg Møller, Brønshøj, all of Denmark

[73] Assignees: Novartis Finance Corporation, New York, N.Y.; Royal Veterinary Agricultural University, Copenhagen, Denmark

[21] Appl. No.: 656,177

[22] PCT Filed: Nov. 28, 1994

[86] PCT No.: PCT/EP94/03938

§ 371 Date: Aug. 8, 1996

§ 102(e) Date: Aug. 8, 1996

[87] PCT Pub. No.: WO95/16041

PCT Pub. Date: Jun. 15, 1995

[30]     Foreign Application Priority Data

Dec. 8, 1993   [EP]   European Pat. Off. .............. 93810860

[51] Int. Cl.$^6$ .............................. C12Q 1/00; C12Q 1/26; G01N 33/53; C07H 19/00
[52] U.S. Cl. .................. 435/4; 435/7.1; 435/25; 536/22.1
[58] Field of Search ............................ 536/22.1; 435/7.1, 435/4, 25; 800/205

[56]           References Cited
FOREIGN PATENT DOCUMENTS

| | | |
|---|---|---|
| 0 281 245 A2 | 2/1988 | European Pat. Off. . |
| 0 522 880 A3 | 7/1992 | European Pat. Off. . |
| WO 91/10745 | 1/1991 | WIPO . |
| WO 93/04174 | 8/1992 | WIPO . |
| WO 93/21326 | 4/1993 | WIPO . |

OTHER PUBLICATIONS

Gabriac, et al., "Purification and Immunocharacterization of a Plant Cytochrome P450: The Cinnamic Acid 4–Hydroxylase", *Archives of Biochemistry and Biophysics*, 288(1): 302–309 (1991).

Halkier, et al., "The Biosynthesis of Cyanogenic Glucosides in Higher Plants", *The Journal of Biological Chemistry*, 264(33): 19487–19494 (1989).

Halkier, et al., "Biosynthesis of theCyanogenic Glucoside Dhurrin in Seedlings of *Sorghum bicolor* (L.) Moench and Partial Purification of the Enzyme System Involved", *Plant Physiol.*, 90: 1552–1559 (1989).

Halkier, et al., "Cyanogenic glucosides: the biosynthetic pathway and the enzyme system involved", *Department of Plant Physioology, Royal Veterinary and Agricultural University*, 40: 49–66 (1988).

Halkier, et al., "The Biosynthesis of Cyanogenic Glucosides in Higher Plants", *The Journal of Biological Chemistry*, 265(34): 21114–21121 (1990).

Halkier, et al., "Involvement of Cytochrome P–450 in the Biosynthesis of Dhurrin in *Sorghum bicolor* (L.) Moench", *Plant Physiol.*, 96: 10–17 (1991).

Halkier, et al., "2–Nitro–3–(p–hydroxyphenyl)propionate and aci–1–nitro–2–(p–hydroxyphenyl)ethane, two intermediates in the biosynthesis of the cyanogenic glucoside dhurrin in *Sorghum bicolor* (L.) Moench", *Proc. Natl. Acad. Sci.*, 88: 487–491 (1991).

Koch, et al., "The biosynthesis of cyanogenic glucosides in seedlings of cassava (*Manihot esculenta* Crantez).", *Archives of Biochemistry and Biophysics*, 292: 141–150 (1992).

Sibbesen et al., "Purification of the Hydroxylating Enzyme System Involved in the Biosynthesis of the Cyanogenic Glucoside Dhurrin in *Sorghum Bicolor* (l.) Moench", *Biochemistry and Biophysics of Cytochrome P450*, 232 (1991).

*Primary Examiner*—Ardin H. Marschel
*Assistant Examiner*—Jezia Riley
*Attorney, Agent, or Firm*—J. Timothy Meigs; Gary M. Pace

[57]         ABSTRACT

New cytochrome P-450 dependent monooxygenases and DNA molecules encoding these monooxygenases are provided, which are able to catalyze the biosynthetic pathway from amino acids to their corresponding cyanohydrins, the presursors of the cyanogenic glycosides, or to glucosinolates. Moreover, the invention provides methods for obtaining DNA molecules according to the invention and methods for obtaining transgenic plants resistant to insects, acarids, or nematodes or plants with improved nutritive value.

42 Claims, No Drawings

CYTOCHROME P-450 MONOOXYGENASES

This application is a § 371 of PCT/EP94/03938, filed on Nov. 28, 1994, and published on Jun. 15, 1995, as WO 95/16041, which claims priority of European Patent Application No. 93810860.2, filed on Dec. 8, 1993.

The present invention relates to genetic engineering in plants using recombinant DNA technology in general and to enzymes involved in the biosynthesis of cyanogenic glycosides and glucosinolates and genes encoding these enzymes in particular. The proteins and genes according to the invention can be used to improve the nutritive value or pest resistance of plants.

Cyanogenic glycosides constitute secondary plant metabolites in more than 2000 plant species. In some instances they are the source of HCN which can render a plant toxic if it is taken as food. For example the tubers of the cyanogenic crop cassava (Manihot esculenta) constitute an important staple food in tropical areas. However, the cyanogenic glycosides present in the tubers may cause cyanide poisoning in humans due to insufficiently processed cassava products. Other plant species whose enzymatic production of HCN accounts for their potential toxicity if taken in excess as food or used as animal feed include white clover (Trifolium repens), sorghum (Sorghum bicolor), linen flax (Linum usitatissimum), triglochinin (Triglochin maritima), lima beans (Phaseolus lunatus), almonds (Amygdalus) and seeds of apricot (Prunus), cherries and apple (Malus). The toxic properties could be reduced by blocking the biosynthesis of cyanogenic glycosides in these plants.

The primary precursors of the naturally occuring cyanogenic glycosides are restricted to the five hydrophobic protein amino acids valine, leucine, isoleucine, phenylalanine and tyrosine and to a single non-protein amino acid, cyclopentenylglycine. These amino acids are converted in a series of reactions to cyanohydrins which are ultimately linked to a sugar residue. Amygdalin for example constitutes the O-β-gentiobioside and prunasin the O-β-glucoside of (R)-mandelonitrile. Another example of cyanogenic glycosides having aromatic aglycones is the epimeric pair of the cyanogenic glycosides dhurrin and taxiphyllin which are to be found in the genus Sorghum and Taxus, respectively. p-Hydroxymandelo-nitrile for example is converted into dhurrin by a UDPG-glycosyltransferase. Similiar glycosyltransferases are believed to be present in most plants. Vicianin and lucumin are further examples for disaccharide derivatives similiar to amygdalin. Sambunigrin contains (S)-mandelonitrile as its aglycone and is therefore epimeric to prunasin.

Examples of cyanogenic glycosides having aliphatic aglycones are linamarin and lotaustralin found in clover, linen flax, cassava and beans. A detailed review on cyanogenic glycosides and their biosynthesis can be found in Conn, Naturwissenschaften 66:28–34, 1979, herein incorporated by reference.

The biosynthetic pathway for the cyanogenic glucoside dhurrin derived from tyrosine has been extensively studied (Halkier et al, 'Cyanogenic glucosides: the biosynthetic pathway and the enzyme system involved' in: 'Cyanide compounds in biology', Wiley Chichester (Ciba Foundation Symposium 140), pages 49–66, 1988; Halkier and Moller, Plant Physiol. 90:1552–1559, 1989; Halkier et al, The J. of Biol. Chem. 264:19487–19494, 1989; Halkier and Moller, Plant Physiol. 96:10–17, 1990, Halkier and Moller, The J. of Biol. Chem. 265:21114–21121, 1990; Halkier et al, Proc. Natl. Acad. Sci. USA 88:487–491, 1991; Sibbesen et al, in: 'Biochemistry and Biophysics of cytochrome P-450. Structure and Function, Biotechnological and Ecological Aspects', Archakov, A. I. (ed.), 1991, Koch et al, 8th Int. Conf. on Cytochrome P450, Abstract PII.053; and Sibbesen et al, 8th Int. Conf. on Cytochrome P450, Abstract PII.016). It has been found that L-Tyrosine is converted to p-hydroxymandelonitrile, the precursor of dhurrin with N-hydroxytyrosine and supposedly N,N-dihydroxytyrosine, 2-nitroso-3-(p-hydroxyphenyl)propionic acid, (E)- and (Z)-p-hydroxyphenylacetaldehyd oxime, and p-hydroxyphenylacetonitrile as key intermediates. Two monooxygenases dependent on cytochrome P-450 have been reported to be involved in this pathway. A similiar pathway also involving cytochrome P-450 dependent monooxygenases has been demonstrated for the synthesis of linamarin and lotaustrain from valine and isoleucine respectively in cassava (Koch et al, Archives of Biochemistry and Biophysics, 292:141–150, 1992).

It has now surprisingly been found that the complex pathway from L-tyrosine to p-hydroxy-mandelonitrile summarized above can be reconstituted by two enzymes only, which turn out to be identical to the cytochrome P-450 dependent monooxygenases. This result is very surprising given the high degree of complexity of the pathway reflected by its numerous intermediates. Thus the two cytochrome P-450 monooxygenases are multifunctional. A first enzyme, designated P-450$_I$, converts the parent amino acid to the oxime. A second enzyme, designated P-450$_{II}$, converts the oxime to the cyanohydrin. Multifunctional cytochrome P-450 enzymes have not previously been found and described in plants.

Glucosinolates are hydrophilic, non-volatile thioglycosides found within several orders of dicotyledoneous angiosperms (Cronquist, 'The Evolution and Classification of Flowering Plants, New York Botanical Garden, Bronx, 1988). Of greatest economic significance is their presence in all members of the Brassicaceae (order of Capparales), whose many cultivars have for centuries provided mankind with a source of condiments, relishes, salad crops and vegetables as well as fodders and forage crops. More recently, rape (especially Brassica napus and Brassica campestris) has emerged as a major oil seed of commerce. About 100 different glucosinolates are known possessing the same general structure but differing in the nature of the side chain. Glucosinolates are formed from protein amino acids either directly or after a single or multiple chain extension (Underhill et al, Biochem. Soc. Symp. 38:303–326, 1973). N-hydroxy amino acids and aldoximes which have been identified as intermediates in the biosynthesis of cyanogenic glycosides also serve as efficient precursors for the biosynthesis of glucosinolates (Kindl et al, Phytochemistry 7:745–756, 1968; Matsuo et al, Phytochemistry 11:697–701, 1972; Underhill, Eur. J. Biochem. 2:61–63, 1967).

It has now surprisingly been found that the cytochrome P-450$_I$ involved in cyanogenic glycoside synthesis is very similiar to the corresponding biosynthetic enzyme in glucosinolate synthesis.

The reduction of the complex biosynthetic pathway for cyanohydrins described above to the catalytic activity of only two enzymes, cytochrome P-450$_I$ and P-450$_{II}$, allows the introduction of the biosynthetic pathway of dhurrin into plants, which plants in their wildtype phenotype do not normally produce cyanogenic glycosides. By transfection of gene constructs coding for one or both of the two cytochrome P-450 monooxygenases it will be possible to either reconstitute or newly establish a biosynthetic pathway for cyanogenic glycosides. It is therefore an object of the present invention to provide genes coding for cytochrome P-450 monooxygenases active in the biosynthesis of cyanogenic glycosides.

The introduction of a biosynthetic pathway for cyanogenic glycosides into plants by methods known in the art, which in their wildtype phenotype do not express these glycosides is of great interest. This is due to the surprising finding of the present invention that cyanogenic glycosides can be toxic to insects, acarids, and nematodes. Therefore, the introduction or reconstitution of a biosynthetic pathway for cyanogenic glycosides in plants or certain plant tissues will allow to render plants toxic to insects, acarids or nematodes and thus help to reduce the damage to the crop by pests. In combination with other insecticidal principles such as *Bacillus thuringiensis* endotoxins the damage to the crop by pests could be even further reduced.

Alternatively, the sequences of the genes encoding the monooxygenases according to the invention can be used to design DNA plasmids which upon transfection into a plant containing cyanogenic glycosides such as cassava, sorghum or barley eliminate cyanogenic glycosides normally produced in wildtype plants. This can be achieved by expression of antisense or sense RNA or of ribozymes as described in EP-458 367 A1, EP-240 208-A2, U.S. Pat. No. 5,231,020, WO 89/05852, and WO 90/11682 which RNA inhibits the expression of monooxygenases according to the invention. This is of great interest as in spite of numerous efforts it has not been possible through traditional plant breeding to completely remove the cyanogenic glycosides from for example cassava and sorghum. On the other hand it has been shown that elevated amounts of cyanogenic glycosides in the epidermal cells of barley cultivars confer increased sensitivity to attack by the mildew fungus *Erysiphe graminis* (Pourmohensi, PhD thesis, Göttingen, 1989; Ibenthal et al, Angew. Bot. 67:97–106, 1993). A similiar effect has been observed in the cyanogenic rubber tree *Hevea brasiliensis* upon attack by the fungus *Microcyclus ulei* (Lieberei et al, Plant Phys. 90:3–36, 1989) and with flax attacked by *Colletotrichum lini* (Lüdtke et al, Biochem. Z. 324:433–442, 1953). In these instances the quantitative resistance of the plants stipulated above and of other plants, where cyanogenic glycosides confer increased sensitivity to attack by microorganisms, can be increased by preventing the production of cyanogenic glycosides in such plants. In barley, the cyanogenic glycosides are located in the epidermal cells. The antisene, sense or ribozyme constructs are therefore preferably but but not necessarily combined with an epidermis specific promoter.

The presence of even minor amounts of cyanogenic glycosides in plants may also cause nutritional problems due to generation of unwanted carcinogens as demonstrated in barley. Barley malt for example contains low amounts of the cyanogenic glucoside epiheterodendrin which in the cause of production of grain-based spirits can be converted to ethylcarbamate which is considered to be a carcinogen. Attempts are being made to introduce mandatory maximum allowable concentrations of ethylcarbamate in fermented food, beverages and spirits (Food Chemical News 29:33.35, 1988).

Plants containing cyanogenic glycosides typically contain only a single cyanogenic glycoside or just a few. In certain cases it is of interest to alter the cyanogenic glycoside profile of a plant. Since cytochrome P-$450_{II}$ shows broad substrate specificity this enzyme typically converts the aldoxime produced by cytochrome P-$450_{I}$ into the corresponding cyanohydrin. Alteration of the chemical identity of cyanogenic glycosides produced in a specific plant can thus be accomplished by transforming a plant with an additional gene encoding an expressible cytochrome P-$450_{I}$ monooxygenase with a substrate specificity different from the naturally occuring enzyme.

The present invention relates primarily to a DNA molecule coding for a cytochrome P-450 monooxygenase, which catalyzes the conversion of an amino acid to the corresponding N-hydroxyamino acid and the oxime derived from this N-hydroxyamino acid. Preferably the inventive monooxygenase catalyzes the conversion of an amino acid selected from the group consisting of tyrosine, phenylalanine, tryptophan, valine, leucine, isoleucine and cyclopentenylglycine or an amino acid selected from the group consisting of L-tyrosine, L-valine and L-isoleucine. Additionally the present invention relates to a DNA molecule coding for a cytochrome P-450 monooxygenase, which monooxygenase catalyzes the conversion of said oxime to a nitrile and the conversion of said nitrile to the corresponding cyanohydrin. The DNA molecules according to the invention either correspond to naturally occuring genes or to functional homologues thereof which are the result of mutation, deletion, truncation, etc. but still encode cytochrome P-450 monooxygenases, which either catalyze the conversion of an amino acid to the corresponding N-hydroxyamino acid and the oxime derived from this N-hydroxyamino acid, or the conversion of said oxime to a nitrile and the subsequent conversion of said nitrile to the corresponding cyanohydrin. Both monooxygenases are able to catalyze more than one reaction of the biosynthetic pathway of cyanogenic glycosides but preferably contain a single catalytic center. The monooxygenase cytochrome P-$450_{I}$ converting the parent amino acid is also involved in glucosinolate biosynthesis. Because cytochrome P-$450_{I}$ determines the substrate specificity and thus the type of glucosinolates produced and because cytochrome P-$450_{I}$ constitutes the rate limiting step, the principles already described above for cyanogenic glucosides can also be used to down- or up-regulate the synthesis of glucosinolates in glucosinolate producing plants and to alter the compositon of glucosinolates produced.

The inventive DNA molecule encoding cytochrome P-$450_{I}$ is obtainable from plants which produce cyanogenic glycosides and glucosinolates. These plants include but are not limited to plants selected from the group consisting of the species Sorghum, Trifolium, Linum, Taxus, Triglochin, Mannihot, Amygdalus and Prunus as well as cruciferous plants. In a preferred embodiment of the invention the DNA molecule is obtained from *Sorghum bicolor* (L.) Moench or *Manihot esculenta* Crantz. The sequence similarity between cytochrome P-$450_{I}$ monooxygenases from different plants producing cyanogenic glycosides or glucosinolates is evidenced by the specific cross-reactivity of antibodies prepared against cytochrome P-$450_{TYR}$ isolated from sorghum, with the corresponding cytochrome P-450 enzyme in cassava and with the corresponding enzyme in the glucosinolate producing plant *Tropaeolum majus*. Southern blotting using the cDNA clone encoding cytochrome P-$450_{TYR}$ shows specific and strong hybridization to genomic DNA isolated from cassava, *Tropaeolum majus*, and rape. Of all approximately 250 known published sequences for cytochrome P-450 enzymes, cytochrome P-$450_{TYR}$ shows the highest sequence similarity to the petunia 3'5'-flavonoid hydroxylase (30,8%) and 28% sequence similiarity to CYP1A2 from rabbit. The group of cytochrome P-$450_{I}$ monooxygenases functionally characterized by catalyzing the conversion of an amino acid to the corresponding aldoxime can thus be defined as cytochrome P-450 enzymes the amino acid sequence of which exhibits a 32% or higher sequence similarity and preferably a 40% or higher sequence similarity to that of cytochrome P-450$_{TYR}$. Cytochrome P-450 gene protein families are defined as having less than 40% amino acid identity to a cytochrome P-450 protein from any other family. Consequently, cytochrome P-450$_{TYR}$ belongs to a new P-450 protein family.

The inventive DNA molecule encoding cytochrome P-450$_{II}$ is obtainable from plants which produce cyanogenic glycosides. In a preferred embodiment of the invention the DNA molecule is obtained from *Sorghum bicolor* (L.) Moench or *Manihot esculenta* Crantz. The enzyme isolated from *Sorghum bicolor* (L.) Moench is designated cytochrome P-450$_{Ox}$. The catalytic properties of this enzyme resembles those of a cytochrome P-450 activity reported in microsomes from rat liver (DeMaster et al, J. Org. Chem. 5074–5075, 1992) which has neither been isolated nor further characterized. A characteristic of cytochrome P-450$_{Ox}$ and of other members belonging to the cytochrome P-450$_{Ox}$ family is that dehydration of the oxime to the corresponding nitrile is dependent on the presence of NADPH but that this dependence can be overcome by the addition of sodium dithionite or other reductants. Cytochrome P-450 enzymes able to convert aldoximes into cyanohydrins might be present in most living organisms.

For the purposes of gene manipulation using recombinant DNA technology the DNA molecule according to the invention may in addition to the gene coding for the monooxygenase comprise DNA which allows for example replication and selection of the inventive DNA in microorganisms such as *E. coli*, Bacillus, Agrobacterium, Streptomyces or yeast. It may also comprise DNA which allows the monooxygenase genes to be expressed and selected in homologous or heterologous plants. Such sequences comprise but are not limited to genes whose codon usage has been adapted to the codon usage of the heterologous plant as described in WO 93/07278; to genes conferring resistance to neomycin, kanamycin, methotrexate, hygromycin, bleomycin, streptomycin, or gentamycin, to aminoethylcystein, glyophosphate, sulfonylurea, or phosphinotricin; to scorable marker genes such as galactosidase; to its natural promoter and transcription termination signals; to promoter elements such as the 35S and 19S CaMV promoters, or tissue specific plant promoters such as promoters specific for root (described for example in EP-452 269-A2, WO 91/13992, U.S. Pat. No. 5,023,179), green leaves such as the maize phosphoenol pyruvate carboxylase (PEPC), pith or pollen (described for example in WO 93/07278), or inducible plant promoters (EP 332 104); and to heterologous transcription termination signals.

The present invention also relates to monooxygenases which catalyze the conversion of an amino acid preferably selected from the group consisting of tyrosine, phenylalanine, tryptophan, valine, leucine, isoleucine and cyclopentenylglycine to the corresponding N-hydroxyamino acid and the oxime derived from this N-hydroxyamino acid (cytochrome P-450$_I$); or the conversion of said oxime to a nitrile and the conversion of said nitrile to the corresponding cyanohydrine (cytochrome P-450$_{II}$). In a preferred embodiment of the invention the monooxygenases are purified and can be used to establish monoclonal or polyclonal antibodies which specifically bind to the monooxygenases.

In another preferred embodiment of the invention the cytochrome P-450$_{II}$ monooxygenase can be isolated from Sorghum, has a molecular weight of 51 kD as determined by SDS-PAGE and comprises the N-terminal sequence

MDLADIPKQQRLMAGNALVV    (SEQ ID NO: 12).

For other cytochrome P-450$_{II}$ enzymes, the N-terminal sequences may be different.

Optionally, a P-450$_{II}$ monooxygenase might also comprise one of the following sequences:

| | |
|---|---|
| —ARLAEIFATII— | (SEQ ID NO:13) |
| —EDFTVTTK— | (SEQ ID NO: 14) |
| —QYAALGSVFTVPII— | (SEQ ID NO: 15) |

—XXPFPI—(SEQ ID NO: 16).

Another embodiment of the present invention deals with a method for the preparation of cDNA coding for a cytochrome P-450 monooxygenase, which either catalyzes the conversion of an amino acid preferably selected from the group consisting of tyrosine, phenylalanine, tryptophan, valine, leucine, isoleucine and cyclopentenylglycine, to the corresponding N-hydroxyamino acid and the oxime derived from this N-hydroxyamino acid (cytochrome P-450$_I$); or the conversion of said oxime to a nitrile and the conversion of said nitrile to the corresponding cyanohydrin (cytochrome P-450$_{II}$); comprising (a) isolating and solubilizing microsomes from plant tissue producing cyanogenic glycosides or glucosinolates, (b) purifying the cytochrome P-450 monooxygenase, (c) raising antibodies against the purified monooxygenase, (d) probing a cDNA expression library of plant tissue producing cyanogenic glycosides or glycosinolates with said antibody, and (e) isolating clones which express the monooxygenase.

Microsomes can be isolated from plant tissues which show a high activity of the enzyme system responsible for biosynthesis of the cyanogenic glycosides. These tissues may be different from plant species to plant species. A preferred source of microsomes are freshly isolated shoots harvested 1 to 20 days, preferably 2 to 10 days and most preferably 2 to 4 days after germination. Etiolated seedlings are preferred from plant producing cyanogenic glycosides but light grown seedlings may also be used. Following isolation the microsomes are solubilized in buffer containing one or more detergents. Preferred detergents are RENEX 690 (J. Lorentzen A/S, Kvistgard, Denmark), reduced Triton X-100 (RIX-100) and CHAPS.

The cytochrome P-450 monooxygenases can be purified applying standard techniques for protein purification such as ultracentrifugation, fractionated precipitation, dialysis, SDS-PAGE and column chromatography. Possible columns comprise but are not limited to ion exchange columns such as DEAE Sepharose, Reactive dye columns such as Cibacron yellow 3 agarose, Cibacron blue agarose and Reactive red 120 agarose, and gel filtration columns such as Sephacryl S-1000. The cytochrome P-450 content of the individual fractions can be determined from carbon monoxide difference spectra.

The purified proteins can be used to elicit antibodies in for example mice, goats, sheeps, rabbits or chickens upon injection. 5 to 50 µg of protein are injected several times during approximately 14 day intervals. In a preferred embodiment of the invention 10 to 20 µg are injected 2 to 6 times in 14 day intervals. Injections can be done in the presence or absence of adjuvants. Inmunoglobulins are purified from the antisera and spleens can be used for hybridoma fusion as described in Harlow and Lane, 'Antibodies: A Laboratory Manual', Cold Spring Harbor Laboratory, Cold Spring Harbor, N.Y., 1988, herein incorporated by reference. Antibodies specifically binding to a cytochrome P-450 monooxygenase can also be used in plant breeding to detect plants producing altered amounts of cytochrome P-450 monooxygenases and thus altered amounts of cyanogenic glycosides.

The methods for the preparation of plant tissue cDNA libraries are extensively described in Sambrook et al, Molecular cloning: A laboratory manual. Cold Spring Harbor Laboratory Press, Cold Spring Harbor, N.Y., 1989, the essential parts of which regarding preparation of cDNA libraries are herein incorporated by reference. PolyA$^+$ RNA is isolated from plant tissue which shows a high activity of the enzyme system responsible for biosynthesis of the cyanogenic glycosides or glucosinolates. These tissues may be different from plant species to plant species. A preferred tissue for polyA$^+$ RNA isolation is the tissue of freshly isolated shoots harvested 1 to 20 days, preferably 2 to 10 days and most preferably 2 to 4 days after germination. When cDNA libraries are made from glucosinolate producing plants older or mature plant tissue may also be used. The obtained cDNA libraries can be probed with antibodies specifically binding the cytochrome P-450 monooxygenase and clones expressing the monooxygenase can be isolated.

An alternative method for the preparation of cDNA coding for a cytochrome P-450 monooxygenase comprises (a) isolating and solubilizing microsomes from plant tissue producing cyanogenic glycosides or glucosinolates, (b) purifying the cytochrome P-450 monooxygenase, (c) obtaining a complete or partial protein sequence of the monooxygenase, (d) designing oligonucleotides specifying DNA coding for 4 to 15 amino acids of said monooxygenase protein sequence (e) probing a cDNA library of plant tissue producing cyanogenic glycosides or glucosinolates with said oligonucleotides, or DNA molecules obtained from PCR amplification of cDNA using said oligonucleotides, and (f) isolating clones which encode cytochrome P-450 monooxygenase.

Amino acid sequences of internal peptides which are the result of protease digestion can be obtained by standard techniques such as Edman degradation. Oligonucleotides specifying DNA coding for partial protein sequences of the inventive monooxygenases are obtained by reverse translation of parts of the protein sequence according to the genetic code. Protein sequences encoded by DNA sequences of low degeneracy are preferred for reverse translation. Their length ranges from 4 to 15 and preferably from 5 to 10 amino acids. If necessary the codons used in the oligonucleotides can be adapted to the codon usage of the plant source (Murray et al, Nucleic Acids Research 17:477–498, 1989). The obtained oligonucleotides can be used to probe cDNA libraries as described in Sambrook et al, Molecular cloning: A laboratory manual. Cold Spring Harbor Laboratory Press, Cold Spring Harbor, N.Y., 1989, for clones which are able to basepair with said oligonucleotides. Alternatively, oligonucleotides can be used in a polymerase chain reaction, the methodology of which is known in the art, with plant cDNA as the template for amplification. In this case the obtained amplification products are used to probe the cDNA libraries. Clones encoding cytochrome P-450 monooxygenases are isolated.

An alternative method of cloning genes is based on the construction of a gene library composed of expression vectors. In that method, analogously to the methods already described above, genomic DNA, but preferably cDNA, is first isolated from a cell or a tissue capable of expressing a desired gene product—in the present case a P-450 monooxygenase—and is then spliced into a suitable expression vector. The gene libraries so produced can then be screened using suitable measures, preferably using antibodies, and those clones selected which comprise the desired gene or at least part of that gene as an insert.

Alternatively, total DNA from the DNA library, preferably from the cDNA library, can be prepared and used as a template for a PCR reaction with primers representing low degeneracy portions of the amino acid sequence. Preferably, the primers used will generate PCR products that represent a significant portion of the nucleotide sequence. The PCR products can be further probed to determine if they correspond to a portion of the P-450 monooxygenase gene using a synthetic oligonucleotide probe corresponding to an amino acid fragment sequence located in the interior or middle region of the P-450 monooxygenase protein.

The cDNA clone s an d PCR products prepared as described above or fragments thereof may be used as a hybridization probe in a process of identifying further DNA sequences from a homologous or a heterologous source organism encoding a protein product that exhibits P-450 monooxygenase activity such as, for example, a fungi or a heterologous plant. A suitable source would be tissue from plants containing cyanogenic glycosides or glucosinolates.

They may also be used as an RFLP marker to determine, for example, the location of the cytochrome P-450 monooxygenase gene or a closely lined trait in the plant genome or for marker assisted breeding [EP-A 306,139; WO 89/07647].

Using the methods described above it is thus possible to isolate a gene that codes for a P-450 monooxygenase.

Genes encoding cytochrome P-450 monooxygenase can be used in a method for producing a purified recombinant cytochrome P-450 monooxygenase which monooxygenase either catalyzes the conversion of an amino acid preferably selected from the group consisting of tyrosine, phenylalanine, tryptophan, valine, leucine, isoleucine and cyclopentenylglycine to the corresponding N-hydroxyamino acid and the oxime derived from this N-hydroxyamino acid; or the conversion of said oxime to a nitrile and the conversion of said nitrile to the corresponding cyanohydrine; comprising (a) engineering the gene encoding said monooxygenase to be expressible in a host organism such as bacteria, yeast or insect cells, (b) transforming said host organism with the engineered gene, and (c) isolating the protein from the host organism or the culture supernatant.

In a preferred embodiment of the invention the method is used to obtain purified recombinant cytochrome P-450$_{TYR}$, P-450$_{Ox}$ or cytochrome P-450$_{TYR}$ which has been modified by known techniques of gene technology. Preferably the modifications lead to increased expression of the recombinant protein or to altered substrate specificity.

The inventive DNA molecules can be used to obtain transgenic plants resistant to insects or acarids examples of which are listed but not limited to those in Table B as well as nematodes. Preferably the transgenic plants are resistant to Coleoptera and Lepidoptera such as western corn root worm (*Diabrotica virgifera virgifera*), northern corn root worm (*Diabrotica longicornis barberi*), southern corn rootworm (*Diabrotica undecimpunctata howardi*), cotton bollworm, European corn borer, corn root webworm, pink bollworm and tobacco budworm. The transgenic plants comprise DNA coding for monooxygenases which catalyze the conversion of an amino acid to the corresponding N-hydroxyamino acid and the oxime derived from this N-hydroxyamino acid; or the conversion of said oxime to a nitrile and the conversion of said nitrile to the corresponding cyanohydrine. In addition the transgenic plants may comprise monooxygenase genes genetically linked to herbicide resistance genes. The transgenic plants are preferably monocotyledoneous or dicotyledoneous plants examples of which ar listed in Table A. Preferably they are selected from the group consisting of maize, rice, wheat, barley, sorghum, cotton, soybeans, sunflower, grasses and oil seed rape. The plants can be obtained by a method comprising (a) introducing into a plant cell or plant tissue which can be regenerated to a complete plant, DNA comprising a gene expressible in that plant encoding an inventive monooxygenase, (b) selecting transgenic plants, and (c) identifying plants which are resistant to insects, acarids, or nematodes.

The inventive DNA molecules can also be used to obtain transgenic plants expressing anti-sense or sense RNA or ribozymes targeted to the genes of the endogenous P-450 monooxygenases the expression of which reduces the expression of cytochrome P-450 monooxygenases. Such plants show improved disease resistance or nutritive value due to reduced expression of cyanogenic glycosides or glucosinolates. The plants can be obtained with a method comprising (a) introducing into a plant cell or tissue which can be regenerated to a complete plant, DNA encoding sense RNA, anti sense RNA or a ribozyme, the expression of which reduces the expression of cytochrome P-450 monooxygenases according to claims 1 or 8, (b) selecting transgenic plants, and (c) identifying plants with improved disease resistance or nutritive value.

A number of very efficient processes are available for introducing DNA into plant cells, which processes are based on the use of gene transfer vectors or on direct gene transfer processes.

One possible method of inserting a gene construct into a cell makes use of the infection of the plant cell with *Agrobacterium tumefaciens* and/or *Agrobacterium rhizogenes*, which has been transformed with the said gene construction. The transgenic plant cells are then cultured under suitable culture conditions known to the person skilled in the art, so that they form shoots and roots and whole plants are finally formed.

Within the scope of this invention is the so-called leaf disk transformation using Agrobacterium (Horsch et al, Science 227:1229–1231, 1985) can also be used. Sterile leaf disks from a suitable target plant are incubated with Agrobacterium cells comprising one of the chimaeric gene constructions according to the invention, and are then transferred into or onto a suitable nutrient medium. Especially suitable, and therefore preferred within the scope of this invention, are LS media that have been solidified by the addition of agar and enriched with one or more of the plant growth regulators customarily used, especially those selected from the group of the auxins consisting of a-naphthylacetic acid, picloram, 2,4,5-trichlorophenoxyacetic acid, 2,4-dichlorophenoxyacetic acid, indole-3-butyric acid, indole-3-lactic acid, indole-3-succinic acid, indole-3-acetic acid and p-chlorophenoxyacetic acid, and from the group of the cytokinins consisting of kinetin, 6-benzyladenine, 2-isopentenyladenine and zeatin. The preferred concentration of auxins and cytokinins is in the range of 0.1 mg/l to 10 mg/l.

After incubation for several days, but preferably after incubation for 2 to 3 days at a temperature of 20° C. to 40° C., preferably from 23° C. to 35° C. and more preferably at 25° C. and in diffuse light, the leaf disks are transferred to a suitable medium for the purpose of shoot induction. Especially preferred for the selection of the transformants is an LS medium that does not contain auxin but contains cytokinin instead, and to which a selective substance has been added. The cultures are kept in the light and are transferred to fresh medium at suitable intervals, but preferably at intervals of one week. Developing green shoots are cut out and cultured further in a medium that induces the shoots to form roots. Especially preferred within the scope of this invention is an LS medium that does not contain auxin or cytokinin but to which a selective substance has been added for the selection of the transformants.

In addition to Agrobacterium-mediated transformation, within the scope of this invention it is possible to use direct transformation methods for the insertion of the gene constructions according to the invention into plant material.

For example, the genetic material contained in a vector can be inserted directly into a plant cell, for example using purely physical procedures, for example by microinjection using finely drawn micropipettes (Neuhaus et al, Theoretical and Applied Genetics 74:363–373, 1987), electroporation (D'Halluin et al, The Plant Cell 4:1495–1505, 1992; WO 92/09696), or preferably by bombarding the cells with microprojectiles that are coated with the transforming DNA ("Microprojectile Bombardment"; Wang et al, Plant Molecular Biology 11:433–439, 1988; Gordon-Kamm et al, The Plant Cell 2:603–618, 1990; McCabe et al, Bio/Technology 11:596–598, 1993; Christou et, Plant Physiol. 87:671–674, 1988; Koziel et al, Biotechnology 11: 194–200, 1993). Moreover, the plant material to be transformed can optionally be pretreated with an osmotically active substance such as sucrose, sorbitol, polyethylene glycol, glucose or mannitol.

Other possible methods for the direct transfer of genetic material into a plant cell comprise the treatment of protoplasts using procedures that modify the plasma membrane, for example polyethylene glycol treatment, heat shock treatment or electroporation, or a combination of those procedures (Shillito et al, Biotechnology 3:1099–1103, 1985).

A further method for the direct introduction of genetic material into plant cells, which is based on purely chemical procedures and which enables the transformation to be carried out very efficiently and rapidly, is described in Negrutiu et al, Plant Molecular Biology 8:363–373, 1987.

Also suitable for the transformation of plant material is direct gene transfer using co-transformation (Schocher et al, Bio/Technology 4:1093–1096, 1986).

The list of possible transformation methods given above by way of example does not claim to be complete and is not intended to limit the subject of the invention in any way.

In another embodiment of the invention target plants are exposed to a pesticidally effective amount of a cyanogenic glycoside to control insects, acarids, or nematodes attacking a monocotyledonous or dicotyledonous plant selected from the group of plant types consisting of Cereals, Protein Crops, Fruit Crops, Vegetables and Tubers, Nuts, Oil Crops, Sugar Crops, Forage and Turf Grasses, Forage Legumes, Fiber Plants and Woody Plants, Drug Crops and Spices and Flavorings.

The following examples further describe the materials and methods used in carrying out the invention and the subsequent results. They are offered by way of illustration, and their recitation should not be considered as a limitation of the claimed invention.

EXAMPLES

Example 1

Preparation of microsomes

Seeds of *Sorghum bicolor* (L.) Moench (hybrid S-1000) are obtained from Seedtec International Inc. (Hereford, Tex.) and germinated in the dark for 2 days at 28° C. on metal screens covered with gauze. Transfer of the seeds to germination trays is carried out under dim green light. Microsomes are prepared from approximately 3 cm tall etiolated seedlings. The seedlings are harvested and homogenized using a mortar and pestle in 2 volumes (v/w) of 250 mM sucrose, 100 mM tricine (pH 7,9), 50 mM NaCl, 2 mM EDTA and 2 mM DTT. Polyvinylpolypyrrolidone is added (0.1 g/g fresh weight) prior to homogenization. The homogenate is filtered through 22 μm nylon cloth and centrifuged 20 minutes at 48000 g. The supernatant is centrifuged for 1 hour at 165000 g. The microsomal pellet is resuspended and homogenized in isolation buffer using a Potter-Elvehjem homogenizer fitted with a teflon pestle. After recentrifugation and rehomogenization, the homogenate is dialyzed overnight against 50 mM Tricine (pH 7,9), 2 mM DTT under a nitrogen atmosphere.

Example 2

Enzyme assays: Determination of total cytochrome P-450

Quantitative determination of total cytochrome P-450 is carried out by difference spectroscopy using an extinction difference coefficient of 91 $mM^{-1}cm^{-1}$ for the complex between reduced cytochrome P-450 and carbon monoxide ($A_{450-490}$) (Omura et al, J. Biol. Chem. 239:2370–2378, 1964). Cytochrome P-450 substrate binding spectra are recorded with stepwise increased substrate concentration until saturating conditions are reached.

Example 3

Purification of cytochrome $P-450_{TYR}$ and $P-450_{Ox}$

| Buffer A | Buffer B | Buffer C |
|---|---|---|
| 8.6% glycerol | 8.6% glycerol | 8.6% glycerol |
| 10 mM $KH_2PO_4/K_2HPO_4$ (pH 7.9) | 40 mM $KH_2PO_4/K_2HPO_4$ (pH 7.9) | 40 mM $KH_2PO_4/K_2HPO_4$ (pH 7.9) |
| 0.20 mM EDTA | 5.0 mM EDTA | 5.0 mM EDTA |
| 2.0 mM DTT | 2.0 mM DTF | 2.0 mM DTT |
| 1.0% RENEX 690 | 1.0% RENEX 690 | 1.0% CHAPS |
| 0.05% RTX-100 | 0.05% RTX-100 | 0.05% RTX-100 |
|  | 0.2% CHAPS |  |

Buffers are degassed three times by stirring in vacuo before detergent and DTT are added. Between each degassing, the buffer is flushed with argon.

Microsomes (400 mg protein in 20 ml) are diluted to 100 ml with a buffer composed of 8.6% glycerol, 10 mM $KH_2PO_4/K_2HPO_4$ (pH 7.9). The microsomes are solubilized by slow addition of 100 ml of the same buffer containing 2% RENEX 690 and 0.2% RTX-100 and constant stirring for 30 minutes. Solubilized cytochrome P-450 is obtained as the supernatant after centrifugation for 30 minutes at 200 000 g in a Beckman 70:Ti rotor. The supernatant (190 ml) is applied (flow rate 100 ml/h) to a column (5×5 cm) of DEAE Sepharose fast flow/S-100 Sepharose (20:80 wet volumes) equilibrated in buffer A. The ion exchange resin DEAE-Sepharose is diluted with the gel filtration material Sephacryl S-100 in the ratio 1:4 to avoid too high concentrations of the cytochrome P-450 enzymes upon binding, which sometimes results in irreversible aggregation. The column is washed with 150 ml buffer A after which the total amount of cytochromes P-450 including cytochrome $P-450_{TYR}$ and cytochrome $P-450_{Ox}$ is eluted with buffer B in a total volume of 150 ml. During this procedure, NADPH-cytochrome P-450-oxidoreductase and Cytochrome $b_5$ remain bound to the column and may subsequently be eluted and separated with buffer B and a gradient of 0–300 mM KCl.

The cytochrome P-450 eluate is adjusted to 1.0% CHAPS, stirred for 30 minutes and then directly applied to a 25 ml (2.6×5 cm) column of Reactive yellow 3 sepharose equilibrated in buffer C+1,0% RENEX 690. The flow rate used is 25 ml/h. The column is washed with buffer C until the absorbance $A_{280}$ shows that RENEX 690 is washed out. Cytochrome $P-450_{TYR}$ does not bind to this column, and is obtained in the run-off and wash. Subsequently the column is eluted with 400 mM KCl in buffer C. The cytochrome $P-450_{Ox}$ containing fractions are combined yielding approximately 60 ml and diluted with 5 volumes of buffer C to lower the KCl strength and permit rebinding of cytochrome $P-450_{Ox}$ on a second Reactive yellow 3 column. This column is eluted with a KCl gradient (0–500 mM) in a total volume of 100 ml in buffer C. This serves to elute cytochrome $P-450_{Ox}$.

The cytochrome $P-450_{Ox}$ pool from the yellow agarose is diluted 5 times with buffer C to 20–25 mM KCl and applied to a Cibachron blue agarose column (0.9×6 cm) equilibrated in buffer C. The flow rate used is 8 ml/h. The column is washed with 20 ml buffer C at the same flow rate. Cytochrome $P-450_{Ox}$ is eluted with a gradient of KCl, 0–2.0M in buffer C in a total volume of 30 ml.

The runoff from the first yellow 3 agarose column is applied (flow rate 40 ml/h) to a column (2.8×8 cm) of Cibachron Blue Agarose equilibrated in buffer C. The column is subsequently washed with buffer C and the cytochrome $P-450_{TYR}$ is eluted with a 0–500 mM linear KCl-gradient (2×100 ml) in buffer C. The combined cytochrome P-450 fractions are diluted 5 times with buffer C and applied (flow rate 7 ml/h) to a column (0.9×5 cm) of Reactive red 120 agarose equilibrated in buffer C. The column is washed with 25 ml buffer C and cytochrome $P-450_{TYR}$ is eluted with a 0–1.0M KCl linear gradient (2×30 ml) in buffer C. Optionally the eluate is gelfiltrated through a Sephadex G-50 column, equilibrated in a buffer composed of 50 mM potassium phosphate (pH 7.9)/400 mM KCl/0.1% CHAPS/2 mM DTT. The eluted cytochrome $P-450_{TYR}$ is dialyzed for 2 hours against 50 mM potassium phosphate (pH 7.9)/2 mM DTT, diluted 4 fold with dialysis buffer in an Amicon ultrafiltration cell fitted with a YM-30 membrane and concentrated to 1.45 nmols/ml.

All procedures are carried out at 4° C. The total cytochrome P-450 content of the individual fractions is determined from the carbon monoxide difference spectrum. The absorption spectrum of the oxidized cytochrome P-450 is also recorded. The presence of a specific cytochrome P-450 is monitored by substrate binding spectra

Example 4

Antibody preparation

Polyclonal antibodies are elicited in rabbits by six repeated subcutaneous injections (approx. 15 μg protein per rabbit per injection) at 15 day intervals of cytochrome $P-450_{TYR}$ or $P-450_{Ox}$ isolated by dye column chromatography or denatured enzyme purified by preparative SDS-PAGE. Freunds complete adjuvant is included in the first injection whereas Freunds incomplete adjuvant is used in subsequent injections. The immunoglobulin fractions of the antisera are purified by ammonium sulfate precipitation (Harboe et al, 'A Manual of Quantitative Immunoelectrophoresis: Methods and Applications', Universitetsforlaget, Oslo, 1973). The antibodies are monospecific as demonstrated by Western blotting.

Example 5

Characterization of P-450$_{TYR}$
5.1. Substrate binding spectra of P-450$_{TYR}$ Cytochrome P-450$_{TYR}$ in the oxidized state has a strong absorption peak at 420 nm, representing the low spin state of the iron of the heme group. The binding of a ligand to the heme group shifts the absorption maximum by changing the spin state of the iron. Binding of tyrosine at the catalytic site of cytochrome P-450$_{TYR}$ induces a change of the spin state of the oxidized iron from low to high spin, and thereby changes the absorption maximum from 420 nm to 390 nm producing a type I spectrum (Jefcoate, Methods in Enzymology 52:258–279, 1978). The following experimental procedure is used to obtain the substrate binding spectrum: two identical cuvettes containing a buffered solution of the isolated cytochrome P-450 are prepared. The substrate of the enzyme is added to the sample cuvette whereas the same volume of buffer is added to the other cuvette. The difference spectrum is then recorded in an SLM-Aminco DW2c spectrophotometer. The absorption difference, A390–420, is proportional to the concentration of cytochrome P-450$_{TYR}$ with a bound substrate at its active site. If a saturating concentration of substrate is added to the sample cuvette, the absorption difference is proportional to the concentration of the substrate specific cytochrome P-450 in the cuvettes. The saturating concentration of the substrate is determined by titrating the cytochrome P-450 sample with increasing amounts of substrate and monitoring $A_{390-420}$.

If a cytochrome P-450 sample can be saturated with two different substrates, there may be two different cytochrome P-450 enzymes in the sample, or there may be one cytochrome P-450 enzyme able to bind to both substrates. To discriminate between these possibilities, saturating amounts of the two substrates are added sequentially and the $A_{390-420}$ absorption change is monitored. If, independent of the order of addition, the addition of the second sample gives rise to an increased $A_{390-420}$ value compared to the value after the addition of the first substrate, the two substrates are bound by different enzymes. If $A_{390-420}$ remains unchanged upon addition of the second substrate, independent of the order of addition, both substrates bind to the same active site, i.e. to the same cytochrome P-450 enzyme. The data shown in Tables C and D below represent results of a typical experiment.

TABLE C

To 500 μl of isolated cytochrome P-450$_{TYR}$ dissolved in 50 mM Tricine pH 7,9 tyrosine is added until saturation concentration is reached followed by addition of N-hydroxytyrosine:

| Added substrate | initial $A_{390-420}$ | dilution factor | resulting $A_{390-420}$ |
|---|---|---|---|
| 30 μl 5 mM tyrosine | 0,0437 | 530/500 | 0,0463 |
| 60 μl 5 mM tyrosine | 0,0496 | 560/500 | 0,0556 |
| 90 μl 5 mM tyrosine | 0,0486 | 590/500 | 0,0573 |
| + 100 μl 20 mM N-hydroxytyrosine | 0,0409 | 690/500 | 0,0564 |

TABLE D

Addtion of N-hydroxytyrosine until saturation concentration is reached, followed by addition of tyrosine

| Added substrate | initial $A_{390-420}$ | dilution factor | resulting $A_{390-420}$ |
|---|---|---|---|
| 50 μl 20 mM N-hydroxytyrosine | 0,0689 | 550/500 | 0,0758 |
| 120 μl 5 mM N-hydroxytyrosine | 0,0919 | 620/500 | 0,1140 |
| 140 μl 5 mM N-hydroxytyrosine | 0,0911 | 640/500 | 0,1166 |
| + 90 μl 5 mM tyrosine | 0,0726 | 730/500 | 0,1060 |

Both tyrosine and N-hydroxytyrosine produce a type I binding spectrum. The data show, that tyrosine and N-hydroxytyrosine bind to the same active site, that is the same cytochrome P-450, thus demonstrating that cytochrome P-450$_{TYR}$ is multifunctional. From the amounts of cytochrome P-450$_{TYR}$ used the absorption coefficient ($\epsilon_{390-420}$) is calculated to be 67 cm$^{-1}$mM$^{-1}$. A complete transition from a low spin state to a high spin state would have resulted in an absorption coefficient of 138 cm$^{-1}$mM$^{-1}$.

5.2. Molecular weight and Amino acid sequence data

The molecular weight of P-450$_{TYR}$ as determined by SDS-PAGE is 57 kD.

Amino acid sequences are obtained by automated Edman degradation. The internal polypeptides are obtained by trypsin digestion of the purified protein and subsequent separation of the peptides using reverse phase HPLC.
N-terminal sequence:

—MATMEVEAAAATVLAAP—   (SEQ ID NO:3)

Internal sequences:

—VWDEPLR—   (SEQ ID NO: 4)

—YVYNLATK—   (SEQ ID NO: 5)

—SDTFMATPLVSSAEPR—   (SEQ ID NO: 6)

—AQSQDITFAAVDNPSNAVEXALAEMVNNPE(SEQ ID NO: 7)

—AQGNPLLTIEEVK—   (SEQ ID NO: 8)

—LVQESDIPK—   (SEQ ID NO: 9)

—ISFSTG—   (SEQ ID NO: 10)

—LPAHLYPSISLH—   (SEQ ID NO: 11)

5.3. Reconstitution of cytochrome P-450$_{TYR}$ activity:

Reconstitution of the enzyme activity of a microsomal P-450 enzyme is accomplished by insertion of the cytochrome P-450 enzyme and the corresponding NADPH-cytochrome P-450 oxidoreductase into appropriate lipid micelles made from different commercially available lipids. Isolation of NADPH-cytochrome P-450 oxidoreductase is done according to Halkier and Moller, Plant Physiol. 96:10–17, 1990. A mixture of lipids can be used but with cytochrome P-450$_{TYR}$ di-lauroyl-phosphatidyl choline (DLPC) provides the best enzymatic activity. One rate limiting factor of this rate limiting reaction is the number of correctly formed complexes of cytochrome P-450$_{TYR}$ and NADPH-cytochrome P-450 oxidoreductase. Excess amounts of the oxidoreductase and concentrated enzyme solutions ensure a sufficient number of active complexes.

A reconstituted enzyme is obtained using the following components:

Cytochrome P-450$_{TYR}$: 100 µg/ml in 50 mM potassium phosphate buffer pH 7,9

Oxidoreductase, purified from *Sorghum bicolor*: 100 µg/ml in 50 mM potassium phosphate buffer pH 7,9

Lipid: 10 mg/ml di-lauroyl-phosphatidyl choline, sonicated in 50 mM potassium phosphate buffer pH 7,9

NADPH: 25 mg/ml H$_2$O $^{14}$C-tyrosine: commercially available from Amersham; [U-$^{14}$C]-L-tyrosine 0.5 µCi 10 µl of the lipid suspension is mixed in a glass vial with 50 µl of the cytochrome P-450$_{TYR}$ (0–1.5 pmol) solution. 50 µl of the oxidoreductase (0–0.15 U) solution is added and then 10 µl tyrosine solution and 10 µl NADPH solution are added and the mixture is sonicated in a Branson 5200 sonication bath for one minute. The reaction mixture is subsequently incubated for 1 hour at 30° C. At the end of the incubation period the reaction is stopped by transferring the glass vials onto ice. Radioactively labelled intermediates formed are extracted into 50 µl ehtyl acetate, applied to a silica coated TLC plate and developed using an ethyl acetate/toluene (1:5 v/v) mixture as mobile phase. The resultant product, p-hydroxyphenylacetaldehyde oxime is visualized by autoradiography of the TLC plate. Alternatively, the intermediates are analyzed by reverse-phase HPLC coupled to a Berthold radioactiviy monitor. The HPLC separation was carried out using a nucleosil 100-10C$_{18}$ column isocratically eluted with 1,5% 2-propanol in 25 mM Hepes pH 7,9 (Halkier et al, J. Biol. Chem. 264:19487–19494, 1989). Control samples may be made by omitting either cytochrome P-450 oxidoreductase or NADPH.

When reconstituted into micelles cytochrome P-450$_{TYR}$ catalyzes the conversion of L-tyrosine all the way to p-hydroxyphenyl-acetaldehyde oxime. The K$_m$ and turnover number of the enzyme are 0.14 mM and 198 min$^{-1}$, respectively, when assayed in the presence of 15 mM NaCl, whereas the values are 0.21 mM and 228 min$^{-1}$ when assayed in the absence of added salt.

The formation of p-hydroxyphenyl-acetaldehyde oxime demonstrates that cytochrome P-450$_{TYR}$ is a multifunctional heme-thiolate protein catalyzing reactions in addition to the initial N-hydroxylation of L-tyrosine. The E/Z ration of the parahydroxyphenyl-acetaldehyde oxime produced by the reconstituted cytochrome P-450$_{TYR}$ and determined by HPLC chromatography is 69/31. Using the TLC/autoradiography system, minute amounts of radiolabelled products comigrating with authentic p-hydroxybenzaldehyde and 1-nitro-2(p-hydroxyphenyl) ethane are detected in the reaction mixtures.

5.4. Inhibitory effect of antibodies against cytochrome P-450$_{TYR}$

The experiments are carried out using monospecific antibodies against P-450$_{TYR}$ as described in section 6.4. which uses antibodies against cytochrome P-450$_{Ox}$. The results are similiar to those obtained with the antibody against cytochrome P-450$_{Ox}$ except that the cytochrome P-450$_{TYR}$ antibody exerts a stronger inhibitory effect (up to 60%) on cyanide production.

5.5. cDNA libraries and colony screening

Poly A$^+$ RNA is isolated from 3 cm high etiolated seedlings of *Sorghum bicolor* (L.) Moench grown as described for seedlings used for preparation of microsomes. The poly A$^+$ RNA is used for the construction of a λgt11 expression library and a λgt10 library. The construction of the libraries can be done according to the procedures described for example in Sambrook et al, Molecular cloning: A laboratory manual. Cold Spring Harbor Laboratory Press, Cold Spring Harbor, N.Y., 1989 or can be ordered by commercial companies such as Strategene (La Jolla, Calif.). Antibodies obtained against cytochrome P450$_{TYR}$ are used to screen the expression libraries as described by Young et al, Procl. Natl. Acad. Sci USA 82:2583–2587. Antigen-antibody complexes are detected enzymatically with alkaline phosphatase-conjugated antibodies (Dakopatts). DNA from 4 positive plaques is prepared according to Grossberger, Nucleic Acid Research 15:6737, 1987. Inserts from λ phages are subcloned into pBluescript II SK (Strategene). Comparison of the deduced amino acid sequence from one of the four inserts with the amino acid sequences obtained from protein sequencing of P450$_{TYR}$ shows that this clone is a partial cDNA clone for P450$_{TYR}$. The partial cDNA clone is used as a probe for a new screen of the λgt10 and λgt11 libraries. The insert sizes of 45 positive clones are determined by southern blotting. Additionally the 45 positive clones are examined for hybridization with two different mixtures of oligonucleotides by southern blotting. The sequences of the oligonucleotide mixtures are based on the partial amino acid sequence data and specify a sequence near the N-terminal end (amino acids 4 to 9) and a sequence near the C-terminal end (amino acids 533–538). Oligonucleotide synthesis is carried out on a Cyclone Plus DNA Synthesizer. Sequencing of one clone derived from the λgt10 library showing the expected size and hybridizing with the two oligonucleotide mixtures shows that the clone is a full-length cDNA clone encoding cytochrome P450$_{TYR}$.

Oligonucleotide specifying amino acids 4 to 9 (MEVEAA) (SEQ ID NO: 17)
5'-ATG-GA[G,A]-GT[C,G,T,A]-GA[G,A]-GC[CGTA]-GC-3'

Oligonucleotide specifying amino acids 533 to 538 (DFTMAT) (SEQ ID NO: 18)
5'-GA[C,T]-AC[C,G,T,A]-TT[C,T]-ATG-GC[C,G,T,A]-AC-3'

5.6. DNA sequencing

DNA sequencing is carried out by the dideoxy chain method (Sanger et al, Proc. Natl. Acad. Sci. USA 74:5463–5467, 1977) using [$^{35}$S]-dATP. T7 DNA polymerase and deoxynucleotides are obtained from Pharmacia, dideoxynucleotides from Boehringer Mannheim. Sequencing of the full-length cDNA clone is done partly by subcloning and partly by using synthetic oligonuecleotides as primers. The oligonucleotide primers can be ordered with commerical companies.

5.7. Southern blotting

λDNA isolated from the positive clones is digested with Eco RI. The inserts are separated from λDNA by electrophoresis on a 0.7% agarose gel. After electrophoresis, DNA is capillary blotted onto a Zetaprobe membrane (Biorad) using 10 mM NaOH for the transfer. Hybridization is performed at 68° C. in 1.5×SSPE (270 mM NaCl, 15 mM Na$_2$HPO$_4$ pH 7.0, 1.5 mM EDTA, 1% sodium dodecyl sulphate) 10% dextransulphate, 0,5% skim milk and 0.1 mg/ml salmon sperm DNA for 16 hours. When the partial cDNA clone is used as probe for hybridization it is labeled with [α-$^{32}$P]dCTP using a random prime labelling kit (Amersham International plc.). The oligonucleotide mixtures are 5'end labeled according to Okkels et al. (Okkels et al, FEBS Letters 237:108–112, 1988). The filters are washed first in 2×SSC (0.9M NaCl, 0.09M trisodium citrate, 0.1% SDS) at 47° C. for 15 min., then in a fresh solution of the same composition at 56° C. for 15 min. and finally in 0.1×SSPE, 0.5% SDS for 30 minutes at 65° C. The presence of radioactively labelled hybridization bands on the filter is monitored by X-ray autoradiography.

5.8. Characterization of a full-length cDNA clone

λDNA isolated from the positive clones is digested with Eco RI. The insert is separated from λDNA by electrophoresis on a 0.7% agarose gel and subcloned into the EcoRI site of the vector pBluescript SK (Strategene) contained within the sequence GCAGGAATTCCGG (SEQ ID NO: 24). The four last bases of this sequence are listed as the first four bases in SEQ ID NO: 1. A clone comprising the described cDNA has been deposited with the Agricultural Research Culture Collection (NRRL), 1815 N. University Street, Peoria, Ill. 61604 U.S.A. under the accession number NRRL B-21168.

The orientation of the insert in the vector is determined as the polylinker restriction site for Pst I being adjacent to the 5'end of the cytochrome P-450 sequence. The sequence of the insert is shown in SEQ ID NO: 1. The sequence comprises an open reading frame (ORF) starting at nucleotide 188 and ending at nucleotide 1861 of SEQ ID NO: 1. It encodes a protein of 558 amino acids and a molecular mass of 61887 Da shown in SEQ ID NO: 2. The sequence comprises the sequences of SEQ ID NO: 3 to SEQ ID NO: 11. The protein is not subject to post-translational modification at the N- and C-terminal ends except for the removal of the N-terminal methionine residue. The N-terminal region of cytochrome P-450$_{TYR}$, however, shows four motifs which in animals are known to target heme-thiolate proteins to the endoplasmatic reticulum.

Searches for sequence similarity are made using the programmes BLAST and FASTA in the nucleotide sequence data bases provided by the EMBL. Pairwise comparisons of cytochrome P-450$_{TYR}$ with other cytochrome P-450 sequences are performed using the programme GAP of the Genetics Computer Group GCG sofware package. Multiple alignments were made using the GCG programme PILEUP.

5.9. Expression of native cytochrome P-450$_{TYR}$ in E. coli

Plasmid pCWOri+ (Gegner et al, Prod. Natl. Acad. Sci. USA 88:750–754, 1991) is used to express the wildtype cytochrome P-450$_{TYR}$ cDNA sequence as described by Barnes et al, Prod. Natl. Acad. Sci. USA 80:5597–5601, 1991. cDNA sequences are introduced into the expression plasmid using polymerase chain reaction (PCR) mutagenesis. A synthetic oligonucleotide (TYROL1b) containing an amino acid-conserving and nucleotide modifying 5' cDNA sequence is used in conjunction with a downstream oligonucleotide (TYROL3) to amplify the N-terminal sequence between the ATG initiator codon (contained within an NdeI site) and a unique BamHI restriction site within the cytochrome P-450$_{TYR}$ sequence. A synthetic oligonucleotide (TYROL2) is used in conjunction with an oligonucleotide (TYROL4) complementary to a unique PstI restriction site to introduce a HindIII restriction site immediately downstream of the TGA stop codon. The expression plasmid pCWtyr is constructed by simultaneous ligation of the 278 basepair PCR NdeI/BamHI fragment, the 1257 basepair BamHI/PstI fragment of cytochrome P-450$_{TYR}$ and the 146 basepair PCR PstI/HindIII fragment with the NdeI/HindIII cleaved vector DNA. E. coli strain JM 109 transformed with plasmid pCWtyr is grown in LB/ampicilline medium at 37° C. Expression of cytochrome P-450$_{TYR}$ is obtained by growing the cells in a medium containing 1 mM isopropyl beta-D-thiogalactopyranoside (IPTG) and shifting the cells to growth at 28° C. at 125 rpm. E. coli produces a functionally active cytochrome P-450$_{TYR}$ enzyme which converts tyrosine into oxime. The analytical procedures are as in the reconstitution experiments described in section 5.3. above. The expressed cDNA clone encoding P-450$_{TYR}$ specifies the synthesis of a single cytochrome P-450 enzyme. Since this enzyme catalyzes the conversion of tyrosine all the way to p-hydroxyphenylacetaldehyde oxime, this unambigeously demonstrates that cytochrome P-450$_{TYR}$ is multifunctional.

The following oligonucleotides are used:

TYROL1b (SEQ ID NO: 19)
5'-CGG GAT CCA TAT GCT GCT GTT ATT AGC AGT TTT TCT GTC GTA-3'

TYROL2 (SEQ ID NO: 20)
5'-GAC CGG CCG AAG CCT TAA TTA GAT GGA GAT GGA-3'

TYROL3 (SEQ ID NO: 21)
5'-AGT GGA TCC AGC GGA ATG CCG GCT T-3'

TYROL4 (SEQ ID NO: 22)
5'-CGT CAT GCT CTT CGG AA-3'

5.10. Expression of truncated and modified cytochrome P-450tyr in E. coli

A modified cytocrome P-450$_{TYR}$, in which the 35 N-terminal amino acids are replaced by the nine N-terminal amino acids from bovine 17α hydroxylase is introduced into the expression vector pSP19g10L which can be obtained from Dr. Henry Barnes (La Jolla, Calif.). This plasmid contains the lac Z promoter fused with the known short leader sequence (g10L) of gene 10 from bacteriophage T$_7$ (Olin et al, 1988). A construct containing the N-terminal amino acids from bovine 17α hydroxylase and a truncated form of the P-450$_{TYR}$ gene is designed using PCR mutagenesis: Oligonucleotide TYROL 1d (5'-CGG GAT CCA TAT GGC TCT GTT ATT AGC AGT TTT TCT GTC GTA CCT GGC CCG-3'; SEQ ID NO 23) containing a 5' mutant cDNA sequence as well as a BamHI and NdeI restriction site is used together with oligonucleotide TYROL 3 comprising the sequence surrounding the unique BamHI restriction site downstream of the ATG start codon of the cDNA coding for P-450$_{TYR}$ to amplify a modified N-terminal sequence of P-450$_{TYR}$. The amplification product is cut with NdeI and BamHI restriction enzymes. To introduce a HindIII site immediately downstream of the stop codon of the P-450$_{TYR}$ gene, oligonucleotides TYROL 2 and TYROL 4 are used in a polymerase chain reaction to obtain a C-terminal fragment of the P-450$_{TYR}$ gene comprising a HindIII restriction site immediately downstream of the stop codon. The amplification product is cut with PstI and HindIII restriction enzymes. The complete expression plasmid is constructed by simultaneous ligation of the N-terminal NdeI/BamHI fragment, the BamHI/PstI fragment of the P-450$_{TYR}$ gene and the C-terminal PstI/HindIII fragment into NdeI/HindIII cleaved pSP19g10L vector DNA. The expression vector obtained is transformed into E. coli strain JM109. Transformed E. coli produce 300 nmol to 500 nmol cytochrome P-450$_{TYR}$ per liter cell culture upon growth at 28° C. in the presence of 1 mM isopropyl-β-D-thiogalactopyranoside and at 125 rpm. Expression levels as high as 900 nmol per liter, equivalent to 55 mg P-450$_{TYR}$ per liter, have been obtained.

Administration of tyrosine to the cell culture results in the production of p-hydroxyphenylacetaldehyde oxime, whereas a cell culture transformed with pSP19g10L alone does not produce the oxime.

Reconstitution experiments with E. cole-expressed cytochrome P-450$_{TYR}$ and sorghum NADPH cytochorme P450 reductase in dilaurylpohsphatidylcholine micelles is performed as described in section 5.3. above. Turnover rates of 349 nmol oxime per nmol P-450$_{TYR}$ per minute can be demonstrated, which is equivalent to the values obtained with sorghum P-450$_{TYR}$.

Purified sorghum cytochrome P-450$_{TYR}$ can be shown to form type I substrate binding spectra with tyrosine and N-hydroxytyrosine (compare section 5.1.). Using P-450$_{TYR}$ expressed in *E. coli* it can be shown that in addition to tyrosine and N-hydroxytyrosine P-450$_{TYR}$ is also able to form a type Ispectrum with p-hydroxyphenylacetaldehyde oxime, 2-nitro-(p-hydroxyphenyl)ethane, p-hydroxyphenylacetonitrile as well as phenylalanine. The molar extinction coefficient E$_{420-390}$ for tyrosine and N-hydroxytyrosine as genuine substrates of P-450$_{TYR}$ are 75.8 cm$^{-1}$mM$^{-1}$ and 64.6 cm$^{-1}$mM$^{-1}$, respectively, whereas the extinction coefficients of the other compounds vary from 20–40 cm$^{-1}$mM$^{-1}$.

Reconstitution experiments using phenylalanine as substrate do not result in the production of the corresponding oxime. This indicates, that cytochrome P-450$_{TYR}$ has a narrow substrate specificity with respect to its enzymatic activity although it is able to bind many tyrosine analogues.

Administration of $^{14}$C-tyrosine directly to *E. coli* cells expressing cytochrome P-450$_{TYR}$ results in the production of p-hydroxyphenylacetaldehyde oxime, indicating that *E. coli* is able to provide the reducing equivalents for cytochrome P-450$_{TYR}$.

The following oligonucleotides are used:
TYROL1d (SEQ ID NO: 23)
  5'-CGG GAT CCA TAT GGC TCT GTT ATT AGC AGT TTT TCT GTC GTA CCT GGC CCG-3'
TYROL2 (SEQ ID NO: 20)
  5'-GAC CGG CCG AAG CTT TAA TTA GAT GGA GAT GGA-3'
TYROL3 (SEQ ID NO: 21)
  5'-AGT GGA TCC AGC GGA ATG CCG GCT T-3'
TYROL4 (SEQ ID NO: 22)
  5'-CGT CAT GCT CTT CGG AA-3'

Example 6

Characterization of P-450$_{Ox}$
6.1. Substrate binding spectra of P450$_{Ox}$

Similiar experiments as reported in section 5.1 are carried out using isolated cytochrome P-450$_{Ox}$ with p-hydroxyphenylacetaldoxime and p-hydroxyphenylacetonitrile as substrate. Cytochrome P-450$_{Ox}$ is found to be multifunctional as P-450$_{TYR}$. Isolated cytochrome P-450$_{Ox}$ resembles the cytochrome P-450 reported to convert oximes to nitriles in rat liver microsomes (DeMaster et al, J. Org. Chem. 5074–5075, 1992).
6.2. Molecular weight and Amino acid sequence data The molecular weight of P-450$_{Ox}$ as determined by SDS-PAGE is 51 kD.

Amino acid sequences are obtained by automated Edman degradation. The internal polypeptides are obtained by trypsin digestion of the purified protein and subsequent separation of peptides using reverse phase HPLC.
N-terminal sequence:

—MDLADIPKQQRLMAGNALVV—   (SEQ ID NO: 12)

Additional peptide sequences:

—ARLAEIFATII—   (SEQ ID NO:13)
  —EDFTVTTK—   (SEQ ID NO:14)
  —QYAALGSVFTVPII—   (SEQ ID NO: 15)
  —XXPFPI—   (SEQ ID NO: 16)

6.3. Reconstitution of cytochrome P-450$_{Ox}$ activity:

The reconstitution assay used for cytochrome P-450$_{Ox}$ is similiar to that used for cytochrome P-450$_{TYR}$ described in section 5.3. A typical assay contains 10 µl DLPC (10 mg/ml); 50 µl cytochrome P-450$_{Ox}$ (24 mg/ml); 50 µl NADPH-cytochrome P-450 oxidoreductase; 20 µl of either 10 mM p-hydroxyphenylacetonitrile or p-hydroxyphenylacetaldehyde oxime; 10 µl NADPH (25 mg/ml); and 60 µl potassium phosphate buffer (pH 7.9).

The reconstitution assay demonstrates that cytochrome P-450$_{Ox}$ converts p-hydroxyphenylacetaldehyde oxime to p-hydroxymandelonitrile. The analytical procedures used are those described for cytochrome P-450$_{TYR}$.
6.4. Inhibitory effect of antibodies against cytochrome P-450$_{Ox}$ The effect of antibodies raised against cytochrome P-450$_{Ox}$ on the biosynthetic activity is measured as the decrease in cyanide production upon incubation of the sorghum microsomes with p-hydroxyphenylacetaldehyde oxime and p-hydroxybenzylcyanide as substrates. The composition of the 150 µl total volume reaction mixtures is: microsomes containing 33 µg protein, 1,5 µmol substrate, 7,5 µmol tricine pH 8,0, 0,33 µmol NADPH, 0–255 µg antibodies and 0–255 µg reference immunoglobulin. The total amount of immunoglobulin in the assay is in each sample adjusted to 225 µg using purified immunoglobulin from a nonimmunized rabbit. The antibodies are preincubated with the microsomes for 15 minute at 30° C. before substrate and NADPH are added. Subsequently the reaction is incubated at 30° C. for 30 minutes. Cyanide is determined by the König reaction (König, Z. Angew. Chem. 18:115, 1905) using methodology described in Halkier and Moller, Plant Physiol. 90:1552–1559, 1989. A value of A$_{680-585}$=1,5 corresponds to 10 nmoles cyanide. Protein concentration was determined using the method of Bradford (Bradford, Anal. Biochem. 72:248–254, 1976). A typical result of such an inhibition experiment is shown in Table E.

TABLE E

| | Substrate p-hydroxyphenylacetaldehyde oxime | | | | | |
|---|---|---|---|---|---|---|
| µg antibody | 0 | 15 | 30 | 60 | 120 | 225 |
| A$_{680-585}$ | 1,00 | 0.96 | 0,92 | 0.87 | 0,88 | 0,66 |
| inhibition | 0% | 4% | 8% | 13% | 12% | 34% |
| A$_{680-555}$ | 1,07 | 1,03 | 1,03 | 0,88 | 0,87 | 0,70 |
| inhibition | 0% | 4% | 4% | 18% | 18% | 35% |

The data show, that the antibody inhibits the reactions to the same extent whichever substrate is added to the microsomal preparation.

Example 7

Induction of glucosinolate production in *Tropaeolum majus*.

Seeds of *Tropaeolum majus* L. cv Empress of India (Dansk Havefroforsyning, Kolding, DK) are allowed to imbibe and germinate in complete darkness for one week at 25° C. In vivo biosynthesis experiments are performed wherein 1 µCi of the tracer $^{14}$C-labelled phenylalanine is administered to excised dark-grown seedlings for 24 hours followed by boiling of the plant material in 90% methanol and analysis of the extracts by HPLC as described by Lykkesfeldt and Moller, 1993. Prior to administration of the tracer to the excised seedling or leaf, the intact plant is subjected to a potential inducer for 24 hours. Administration of 10 mM phenylalanine or 2% ethanol to the vermiculate in which the etiolated seedlings are grown results in a threefold increase in glucosinolate production as compared to control experiments with water. Spraying with 100 µM jasmonic acid followed by incubation for 24 hours results in a fivefold induction in etiolated seedlings and green leaves.

Example 8

Preparation of biosynthetically active microsomes from glucosinolate-producing plant meterial The biosynthetic pathways of glucosinolates, and cyanogenic glucosides share homology by having amino acids as precursors and oximes as intermediates. The assignment of amino acids and oximes as precursors and intermediates in the glucosinolate biosynthetic pathway is based on in vivo experiments demonstrating that these compounds are efficient precursors for glucosinolates. In vitro biosynthetic studies have hitherto not been possible due to the detrimental effect of the degradation products of glucosinolates on enzyme activities. The degradation products are formed upon disruption of the cellular structure. In the disrupted tissue, the glucosinolate-degrading enzyme myrosinase gets in contact with the glucosinolates resulting in the generation of isothiocyanates inactivating the enzymes. We demonstrate that microsomal preparations isolated form one week old plants of either *Sinapis alba* or *Trapaeolum majus* are able to convert tyrosine and phenylalanine, respectively, to the corresponding oximes. The enzymatically active microsomal preparations are obtained by using an isolation buffer fortified with 100 mM ascorbic acid known to inhibit the activity of myrosinase and by inducing the glucosinolate-producing enzyme system prior to the preparation of microsomes. The glucosinolate-producing enzyme systems are induced by taking 7-days-old dark-grown Sinapis plants or 3–4 weeks old light-grown Tropaeolum plants and placing them in the light for 3 days. During this three day period, the young plants are sprayed with 50 $\mu$M jasmonic acid once a day. After 3 days of induction, the plants are harvested and microsomes are prepared as described in section 5.1, except that the homogenisation buffer consists of 250 mM Tricine pH 7.9, 250 mM sucrose, 50 mM sodium bisulfite, 100 mM ascorbic acid, 4 mM DDT, 2 mM EDTA, 1 mM PMSF, and 5 mg/ml BSA. The microsomal preparation is dialysed against homogenization buffer for 1 hour, followed by dialysis against 50 mM Tricine pH 7.9 and 2 mM DTT for another hour.

Example 9

In vitro biosynthesis of oxime by extracts from glucosinolate-containing plants

The microsomal reaction mixture consists of 80 $\mu$l microsomes (10 mg protein per ml), 10 $\mu$l $^{14}$C-phenylalanine (0.5 $\mu$Ci, 464 mCi/mmol, Amersham) or $^{14}$C-tyrosine (0.5 $\mu$Ci, 450 mCi/mmol, Amersham) and 10 $\mu$l NADPH (75 mg/ml). The reaction mixtures are incubated for 1 hour at 37° C. At the end of the incubation period, the reaction mixtures are extracted with 1500 $\mu$l ethyl acetate. The ethyl acetate phase is evaporated to dryness, redissolved in a small volume and analyzed. The production of oximes in the microsomal reaction mixtures can be demonstrated by thin layer chromatography as well as by HPLC analysis as described in section 5.3.

Example 10

Involvement of cytochrome P450-dependent monooxygenases in the glucosinolate pathway Based on the similarity between the first part of the biosynthetic pathways of glucosinolates and cyanogenic glucosides, it was anticipated that the conversion of amino acid to oxime in the glucosinolate pathway is catalyzed by a multifunctional cytochrome P450 monooxygenase homologous to P450$_I$ in the cyanogenic glucoside pathway. In vivo experiments, where radioactively labelled phenylalanine is administered to etiolated tropaeolum seedlings in the presence and absence of 1 mM of the cytochrome P450 inhibitors enilketoconazol and tetcyclacis demonstrate that cytochrome P450 inhibitors cause a reduction of glucosinolate without causing a reduction in the uptake of phenylalanine as measured by ethanol extraction of the plant material. This indicates that the biosynthesis of glucosinolates is dependent on cytochrome P450.

Direct demonstration of the involvment of cytochrome P450 in glucosinolate biosynthesis can be obtained using the in vitro microsomal enzyme system from tropaeolum to demonstrate photoreversible carbon monoxide inhibition of oxime production. The microsomal reaction mixtures are incubated using different experimental conditions. The reaction mixtures are analyzed by HPLC.

| Experimental Condition | % inhibition of oxime production |
|---|---|
| $O_2$ without light | 0 |
| $O_2$ with light | 11 |
| $CO/O_2$ without light | 65 |
| $CO/O_2$ with light | 23 |

The possibility to reactivate the microsomal enzyme system upon irradiation with 450 nm light shows, that the conversion of phenylalanine to the corresponding oxime in the biosynthetic pathway of glucosinolate is dependent on cytochrome P450.

Example 11

Toxicity of cyanogenic glycosides for insects.

Insects or insect larvae are fed on a diet containing added cyanogenic glycoside, a diet containing added cyanogenic glycoside, and callus, or a diet supplemented with the supernatant of callus ground-up in the presence of the cyanogenic glycoside. Mortality is compared to the mortality of insects or insect larvae fed on the diet only.

Example 12

Activity of Amygdalin on larval mortality of Western Corn Root Worm (WCRW):

WCRW larvae are fed on a diet with added amygdalin, a diet with added amygdalin and Black Mexican Sweet (BMS) callus or on a diet supplemented with the supernatant of BMS-callus ground-up in the presence of amygdalin. Larval mortality is compared to the mortality of larvae fed on the diet only.

The results show that amygdalin is lethal in the presence of BMS-callus with an $LC_{50}$ of ~1 mg/ml, and that it is lethal at 2 mg/ml in the absence of BMS-callus. There is significantly less lethality at amygdalin concentrations of less than 1 mg/ml when BMS-callus is absent.

Example 13

Activity of Dhurrin on larval mortality of Western Corn Root Worm (WCRW):

The activity of dhurrin on larval mortality of WCRW was determined as described for amygdalin in example 12.

The results show that the $LC_{50}$ of dhurrin is 368 $\mu$g/ml with 95% confidence limits of 0.28–0.48 $\mu$g/ml. The slope of the regression line is 2.5.

Example 14

Transfection of maize by direct Bombarding of Immature Zygotic Embryos and Isolation of Transformed Callus with the Use of Phosphinothricin as a selection agent.

Immature embryos are obtained approximately 14 days after self-pollination. The immature zygotic embryos are divided among different target plates containing medium capable of inducing and supporting embryogenic callus formation at 36 immature embryos per plate. The immature zygotic embryos are bombarded with plasmids encoding a cytochrome P-450 monooxygenase and a chimeric gene coding for resistance to phosphinothricin using the PDS-1000/He device from DuPont. The plasmids are precipitated onto 1 μm gold particles essentially according DuPont's procedure. Each target plate is shot one time with the plasmid and gold preparation and phosphinothricin is used to select transformed cells in vitro. Selection is applied at 3 mg/l one day after bombardment and maintained for a total of 12 weeks. The embryogenic callus so obtained is regenerated in the absence of the selection agent phosphinothricin. The regenerated plants are tested for their resistance to insects, acarids or nematodes.

Although the foregoing invention has been described in some detail by way of illustration and example for purposes of clarity of understanding, it will be obvious that certain changes and modifications may be practiced within the scope of the appended claims.

TABLE A

PLANT CLASSIFICATION ACCORDING TO USE

CEREALS

Monocot

| | |
|---|---|
| Avena nuda (chinensis) | Chines naked oat |
| A. sativa | Common oats |
| Eleusine coracan | African millet |
| Eragrostis tef | Tef grass |
| Fagopyrum esculentum | Buckwheat |
| F. tataricum | Rye buckwheat |
| Hordeum distichum | Two-row barley |
| H. vulgare | Barley |
| Oryza sativa | Rice |
| Panicum italicium | Italian millet |
| P. miliaceum | Broomcorn millet |
| Pennisetum glaucum | Spiked millet |
| P. spicatum (americanum) | Perl millet |
| Secale cereale | Rye |
| Sorghum vulgare | Grain sorghums |
| X Triticosecale | Triticale |
| Triticum aestivum | Common wheat |
| T. dicoccum | Emmer |
| T. durum | Abyssinian hard wheat |
| T. monococcum | Einkorn wheat |
| Zea mays | Corn, sweet corn |

Dicot

| | |
|---|---|
| Amaranthus paniculatus | Rispenfuchsschwanz |
| Fagopyrum esculentum | Buchweizen |
| F. tataricum | |

PROTEIN CROPS

Dicot

| | |
|---|---|
| Arachis hypogea | Groundnut, peanut |
| Cajanus indicus | Pigeon pea |
| Cicer arietinum | Chickpea |
| Dolichos lablab | Hyacinth bean |
| Glycine gracilis | Manchurian Soya |
| G. max | Soyabean |
| G. ussuriensis | Wild soya |
| Lathyrus sativus | Grass pea |
| Lens culinaris | Lentil |
| Mucuna pruriens | Cowitch, Florida velvet bean |
| Phaseolus acutifolius | Tepary bean |
| P. aureus | Mung, green gram |
| P. lunatus | Lima bean, Sieva |

TABLE A-continued

PLANT CLASSIFICATION ACCORDING TO USE

| | |
|---|---|
| P. coccineus (multiflorus) | Scarlet runner bean |
| P. mungo | Black gram |
| P. vulgaris | French, common, kidney or dwarf bean |
| Vicia faba | Horse bean, broad bean |
| Vigna angularis | Adzuki bean |
| V. sesquipedalis | Asparagus (yard-long bean) |
| V. sinensis | Cowpea |

FRUIT CROPS

Dicot

| | |
|---|---|
| Amygdalus communis | Almond |
| Ananas comosus | Pineapple |
| Artocarpus communis | Breadfruit |
| Carica papaya | Papaya |
| Citrullus vulgaris | Watermelon |
| Citrus grandis | Pummelo |
| C. medica | Citron, lemon |
| C. nobilis | Tangerine |
| C. reticulata | Mandarin |
| C. sinensis | Orange |
| Cydonia oblonga | Quince |
| Diospyros kaki | Japanese persimmon |
| Ficus carica | Fig |
| Fragaria chiloensis | Wild strawberry |
| F. virginiana | Strawberry |
| Litchi chinensis | Litchi |
| Malus asiatica | Chines apple |
| M. pumila | Appple |
| Mangifera indica | Mango |
| Morus rubra | Red mulberry |
| Musa cavendishii | Banana |
| M. paradisiaca | Banana |
| Passiflora edulis | Passion fruit, purple granadilla |
| P. ligularis | Passion flower |
| Persea americana | Avocado pear |
| Phoenix dactylifera | Date palm |
| Prunus armeniaca | Apricot |
| P. avium | Sweet cherry, mazzard |
| P. cerasifera (divaricata) | Cherry plum |
| P. cerasus | Cherry |
| P. domestica | European plum or prune |
| P. maheleb | Maheleb cherry |
| P. persica | Peach and nectarine |
| P. pseudocerasus | Cherry |
| P. salicinia | Japanese peach |
| P. serotina | Wild black cherry |
| Psidium guajava | Guava |
| Punica granatum | Pomegranate |
| Pyrus communis | Pear |
| P. ussuriensis | Chinese pear |
| Ribes grossularia | Gooseberry |
| R. nigrum | Black currant |
| R. rubrum | Red and white currant |
| Rubus idaeus | European raspberry |
| R. strigosus | American raspberry |
| Tamarindus indica | Tamarind |
| Vaccinium angustifolium | Sugarberry |
| V. ashei | Rabbiteye blueberry |
| V. corymbosum | Highbush blueberry |
| V. myrtilloides | Canada blueberry |
| V. oxycoccos | Cranberry |
| Viburnum trilobum | American cranberry bush |
| Vitris labrusca | Fox grape |
| V. vinifera | Grape |

VEGETABLES AND TUBERS

Monocot

| | |
|---|---|
| Allium ascalonicum | Shallot, breen onion |
| A. cepa | Onion |
| A. chinense | Onion |
| A. fistulosum | Welch onion |
| A. porrum | Leek |

TABLE A-continued

PLANT CLASSIFICATION ACCORDING TO USE

| | |
|---|---|
| A. sativum | Garlic |
| A. schoenoprasum | Chives |
| Asparagus officinalis | Asparagus (var. *attilis*) |
| Zea mays | sweet corn |
| Dicot | |
| | |
| Amoracia lapathifolia | Horseradish |
| Apium graveolens | Celery |
| Arabidopsis thaliana | Common wall cress |
| Beta vulgaris | Sugar, mangold or garden beet |
| Brassica alboglabra | Chinese kale |
| B. campestris | Turnip rape |
| B. carinata | Ambyssian mustard |
| B. cernea | Karashina |
| B. chinensis | Chinese mustard or pak-choi |
| B. hirta | White mustard |
| B. juncea | Pai, brown mustard, Indian mustard |
| B. kaber | Charlock |
| B. napobrassica | Swede or rutabaga |
| B. napus | Rape, oil rape, kale |
| B. nigra | Black mustard |
| B. oleracea | Cole, kale, collards, brussels sprouts, cauliflower, cabbage, kohlrabi, broccoli |
| B. pekinensis | Chines cabbage or celery cabbage |
| B. rapa | Turnip |
| Cajanus cajan (*indicus*) | Pigeon pea |
| Canavalia ensiformis | Jack bean |
| Canna edulis | Edible canna |
| Capsicum annuum | Common cultivated pepper |
| C. chinense | Pepper |
| C. frutescens | Cayenne pepper |
| C. pendulum | Pepper |
| C. pubescens | Pepper |
| Cichorium endivia | Endive |
| C. intybus | Chicory |
| Colocasia antiquorum | Taro |
| Crambe maritima | Sea kale |
| Cucumis melo | Melon, cantaloupe |
| C. sativus | Cucumber |
| Cucurbita ficifolia | Malabar gourd |
| C. foetidissima | Calabazilla, buffalo gourd |
| C. maxima | Pumpkin |
| C. moschata | Winter pumpkin |
| C. pepo | Summer squash, vegetable marrow |
| Cynara scolymus | Globe artochoke |
| Daucus carota | Carrot |
| Dioscorea alata | Yarn |
| D. batatas | Chines yarn |
| D. cavennensis | Attoto yam |
| Eruca sativa Mill. | Rocket salad, rocket or roquette |
| Ipomea batatas | Sweet potato |
| Lactuca sativa | Lettuce |
| Lepidium sativum | Garden cress |
| Lycopersicon cerasiforme | Cherry tomato |
| L. esculentum | Tomato |
| Manihot esculenta | Manioc, cassava |
| Nasturtium officinale | Water cress |
| Pastinaca sative | Parsnip |
| Petroselinum crispum (*sativum*) | Parsley |
| Physalis peruviana | Ground cherry |
| Pisum sativum | Pea |
| Raphanus sativus | Radish |
| Rheum officinale | Rhubarb |
| R. rhaponticum | English rhabarb |
| Scorzonera hispanica | Black salsify |
| Sechium edule | Chayote |
| Solanum andigenum | Andean potato |
| S. melongena | Eggplant |
| S. muricatum | Pepino |
| S. phureja | Potato |
| S. tuberosum | Common potato |
| Psinacia oleracea | Spinach |

TABLE A-continued

PLANT CLASSIFICATION ACCORDING TO USE

NUTS

Dicot

| | |
|---|---|
| Anacardium occidentale | Cashew |
| Arachis hypogaea | Peanut |
| Carya illinoinensis | Pecan |
| C. ovata | Shagbark hickory |
| Castanea sativa | Chestnut |
| Covos nucifera | coconut palm |
| Corylus americana | American hazel, filbert |
| C. aveliana | European hazel, cobnut |
| Juglans nigra | Black walnut |
| J. regia | English walnut |
| J. sinensis | Walnut |
| Litchi chinensis | Litchi |
| Macadamia integrifolia | Queensland nut |
| Pistacia vera | Pistachio nut |
| Prunus amygdalus | Almond |

OIL CROPS

Monocot

| | |
|---|---|
| Zea mays | Corn |

Dicot

| | |
|---|---|
| Aleurites cordata | Tung, China wood oil |
| A. moluccana (*triloba*) | Candlenut |
| Arachis hypogea | Ground nut, penut |
| brassica campestris | Rapeseed oil, canola oil |
| B. napus | Rapeseed oil, canona oil |
| Cannabis sativa | Hampseed oil |
| Carthamus tinctorius | Safflower oil |
| Cocos nucifera | Coconut palm |
| Elaeis guineensis | Oil palm |
| Glycine gracilus | Manch, soya |
| G. max | Soybean |
| G. ussuriensis | Wild soya |
| Cossypium hirsutum | Cottonseed oil |
| Helianthus annus | Sunflower |
| Linum usitatissimum | Flax |
| Olea europaea | Olive |
| Papaver somniferum | Poppy seed |
| Ricinus communis | Castor bean |
| Sesamum indicum | Sesame |

SUGAR CROPS

Monocot

| | |
|---|---|
| Saccharum officinarum (*officinarum* x *spontaneum*) | Sugarcane |
| S. robustum | |
| S. sinense | Sugarcane |
| S. spontaneum | Kans grass |
| Sorghum dochna | Sorgo syrup, sugar sorghun |

Dicot

| | |
|---|---|
| Acer saccharum | Sugar maple |
| Beta vulgaris | Sugar or mangold beet |

FORAGE AND TURF GRASSES

Monocot

| | |
|---|---|
| Agropyron cristatum | Crested wheatgrass |
| A. desertorum | Crested wheatgrass |
| A. elongatum | Tall wheatgrass |
| A. intermedium | Intermediate wheatgrass |
| A. smithii | Western wheatgrass |
| A. spicatum | Blue bunch wheatgrass |
| A. trachycaulum | Slender wheatgrass |
| A. trichophorum | Pubescen wheatgrass |
| Alopecurus pratensis | Meadow foxtail |
| Andropogon gerardi | Big bluestem |
| Arrhenatherum elatius | Tall oat grass |

TABLE A-continued

PLANT CLASSIFICATION ACCORDING TO USE

| | |
|---|---|
| *Bothrichloa barbinodis* | Cane blestem |
| *B. ischaemum* | King ranch bluestem |
| *B. saccharoides* | Silver bluestem |
| *Bouteloua curipendula* | Side oats grama |
| *B. eriopoda* | Black grama |
| *B. gracilis* | Blue grama |
| *Bromus erectus* | Upright brome |
| *B. inermis* | Smooth brome |
| *B. riparius* | Meadow brome |
| *Cenchrus ciliaris* | Buffel grass |
| *Chloris gayana* | Rhodes grass |
| *Cymbopogon nardus* | Citronella grass |
| *Cynodon dactylon* | Bermuda grass |
| *Dactylis glomerata* | Cocksfoot |
| *Dichanthium annulatum* | Kleberg bluestem |
| *D. aristatum* | Angleton bluestem |
| *D. sericeum* | Silky bluestem |
| *Digitaria decumbens* | Pangola grass |
| *D. smutsii* | |
| *Elymus angustus* | Altai wild rye |
| *E. junceus* | Russian wild rye |
| *Eragrostis curvula* | Weeping love grass |
| *Festuca arundinacea* | Tall fescue |
| *F. ovina* | Sheeps fescue |
| *F. pratensis* | Meadow fescue |
| *F. rubra* | Red fescue |
| *Lolium multiflorum* | Italian ryegrass |
| *L. perenne* | Perennial ryegrass |
| *Panicum maximum* | Guinea grass |
| *P. purpurascens* | Para grass |
| *P. virgatum* | Switchgrass |
| *Paspalum dilatatum* | Dallis grass, large water grass |
| *P. notatum* | Bahia grass |
| *Pennisetum clandestinum* | Kikuyu grass |
| *P. purpureum* | Dry napier grass |
| *Phalaris arundinacea* | Reed canary grass |
| *Phleum bertolinii* | Timothy |
| *P. pratense* | Timothy |
| *Poa fendleriana* | Mutton grass |
| *P. nemoralis* | Wood meadow grass |
| *P. pratensis* | Kentucky bluegrass |
| *Setaria sphacelata* | Rhodesian timothy |
| *Sorghastrum nutans* | Indian grass |
| *Sorghum halepense* | Johnson grass |
| *S. sudanense* | Sudan grass |
| *Sorghum vulgare* | Great millet |
| FORAGE LEGUMES | |
| Dicot | |
| *Coronilla varia* | Crown vetch |
| *Crotalaria juncea* | Sun hemp |
| *Lespedeza stipulacea* | Korean lespedeza |
| *L. striata* | Common lespedeza |
| *L. sericea* | |
| *Lotus corniculatus* | Birdsfoot trefoil |
| *L. uliginosus* | |
| *Lupinus albus* | Wolf bean, white lupin |
| *L. angustifolius* | Blue lupin |
| *L. luteus* | European yellow lupin |
| *L. mutabilis* | South American lupin |
| *Medicago arabica* | Spotted burr-clover |
| *M. arborea* | Tree alfalfa |
| *M. falcata* | Yellow lucerne |
| *M. hispida* | California burr-clover |
| *M. sativa* | Alfalfa |
| *M. tribuloides* | Barrel medic |
| *Melilotus albus* | White sweet clover |
| *M. officinalis* | Yellow sweet clover |
| *Onobrychis viciifolia* | Sainfoin |
| *Ornithopus sativus* | Serradella |
| *Pueraria thunbergiana* | Kudzu vine |
| *Trifolium alexandrinum* | Egyptian clover |
| *T. augustifolium* | Fineleaf clover |
| *T. diffusum* | Rose clover |
| *T. hybridum* | Alsike clover |
| *T. incarnatum* | Crimson clover |
| *T. ingrescens* | Ball clover |
| *T. pratense* | Red clover |
| *T. repens* | White clover |
| *T. resupinatum* | Persian clover |
| *T. subterraneum* | Subterranean clover |
| *Trigonella foenumgraecum* | Fenugreek |
| *Vicia sative* | Common vetch |
| *V. villosa* | Hairy vetch |
| *V. atropurpurea* | Purple vetch |
| *V. angustifolia* | Narrowleaf vetch |
| *V. dasycarpa* | Wooly pod vetch |
| *V. ervilia* | Monantha (bitter) vetch |
| *V. pannonica* | Hungarian vetch |
| *V. calcarata* | Bard vetch |
| FIBER PLANTS AND WOODY PLANTS | |
| Monocot | |
| *Bambusa vulgaris* | Bamboo |
| Dicot | |
| *Agave sisalana* | Sisal hemp |
| *Boehmeria nivea* | Rhea fiber, ramie |
| *Cannabis indica* | Hemp |
| *C. sativa* | Hemp |
| *Ceiba pentandra* | Silk cotton tree, kapok tree |
| *Corchorus mucronata (striata)* | Hemp |
| *Gossypium arboreum* | Tree cotton |
| *G. barbadense* | Egyptian cotton |
| *G. herbaceum* | Cotton |
| *G. hirsutum* | Upland cotton |
| *G. nanking* | Oriental cotton |
| *Linum angustifolium* | Wild flax |
| *L. usitatissimum* | Flax |
| *Musa textiles* | Manila hemp, abaca |
| DRUG CROPS | |
| Dicot | |
| *Angelica archangelica* | Angelica |
| *Chrysanthemum cinerariifolium* | Palm pyrethrum |
| *Camellia sinensis* | Chinese tea |
| *C. coccineum* | Pyrethrum |
| *Coffea arabica* | Coffee |
| *C. canephora* | Quillow coffee |
| *Cola acuminata* | Kola nut |
| *Nicotiana rustica* | Tobacco |
| *N. tabacum* | Tobacco |
| *Papaver dubium* | Poppy |
| *P. somniferum* | Opium poppy |
| *Theobroma cacao* | cocoa |
| SPICES AND FLAVORINGS | |
| Monocot | |
| *Vanilla fragrans* | Vanilla |
| Dicot | |
| *Artemisa dracunculus* | Tarragon |
| *Cinnamomum zeylanicum* | Cinnamon tree |
| *Hibiscus esculentus* | Okra |
| *Salvia officinalis* | Sage |
| *Thymus vulgaris* | Thyme |
| *Pimpinella anisum* | Anise |
| *Mentha arvensis* | Menthol |
| *M. piperita* | Peppermint |
| *M. viridis* | Spearmint |
| *Coriandrum sativum* | Coriander |

TABLE B

REPRESENTATIVE PLANT PESTS

Coleoptera:

Diabrotica, Melanotus, Agriotes, Limonius, Dalopius, Eleodes, Chaetocnema, Macrodactylus, Sphenophorus, Sitophilus, Lisorhoptrus, Oulema, Rhyzopertha, Prostephanus, Phyllophage, Cyclocephala, Popillia, Anthonomus, Zabrotes, Leptinotarsa Lepidoptera:

Heliothis, Ostrinia, Diatraea, Elasmopalpus, Papaipema, Agrotis, Loxagrotis, Euxoa, *Peridroma saucia*, Chorizagrotis, Spodoptera, Pseudaletia, Chilo, Busseola, Sesamia, Eldana, Maliarpha, Scirpophaga, Duataea, Rupela, *Sitotroga cerealella*, Sitroga, *Plodia interpunctella*, Crambus, Mythimna, Nola, Pectinophora, Acontia, Trichoplusia, Anticarsia, Pseudoplusia, Manduca, Leptinotarsa, Lema Thysanoptera:

Frankliniella, Anaphothrips, Hercothrips, Stenothrips

Homoptera:

Dalbulus, Cicadulina, Rhopalosiphum, Melanaphis, Anuraphis, Prosapia, Nilaparvata, Sogatella, Laodelphax, Sogatodes, Nephotettix, Reciian, Cofana, Empoasca, Poophilus, Schizaphis, Sipha, Paratrioza, Empoasca, Ophilia. Scleroracus, Macrosteles, Circulifer, Aceratagallia, Agallia, Myzus, Macrosiphum, Aphis Diptera:

*Delia platura*, Euxesta, Diopsis, Atherigona, Hydrellia, Orseolia, Chironomus, Contarinia Orthoptera:

Melanoplus, Schistocerca, Sphenarium, Aneolamia

Isoptera:

Microtermes, Macrotermes, Allodontermes, Odontotermes

Heteroptera:

Nezara, Acrosternum, Euschistus, Blissus

Acarina:

Tetranychus, Paratetranychus, Oligonychus

LIST OF REFERENCES CITED

Barnes et al, Prod. Natl. Acad. Sci. USA 80:5597–5601, 1991

Bradford, Anal. Biochem. 72:248–254, 1976

Christou et, Plant Physiol. 87:671–674, 1988

Conn, Naturwissenschaften 66:28–34, 1979

Cronquist, 'The Evolution and Classification of Flowering Plants, New York Botanical Garden, Bronx, 1988

DeMaster et al, J. Org. Chem. 5074–5075, 1992

Food Chemical News 29:33.35, 1988

Gegner et al, Prod. Natl. Acad. Sci. USA 88:750–754, 1991

Grossberger, Nucleic Acid Research 15:6737, 1987

Halkier et al, 'Cyanogenic glucosides: the biosynthetic pathway and the enzyme system involve' in: 'Cyanide compounds in biology', Wiley Chichester (Ciba Foundation Symposium 140), pages 49–66, 1988

Halkier and Moller, Plant Physiol. 90:1552–1559, 1989

Halkier et al, The J. of Biol. Chem. 264:19487–19494, 1989

Halkier and Moller, Plant Physiol. 96:10–17, 1990

Halkier and Moller, The J. of Biol. Chem. 265:21114–21121, 1990

Halkier et al, Proc. Natl. Acad. Sci. USA 88:487–491, 1991

D'Halluin et al, The Plant Cell 4:1495–1505, 1992

Harlow and Lane, 'Antibodies A Laboratory Manual', Cold Spring Harbor Laboratory, 1988

Harboe et al, 'A Manual of Quantitative Immunoelectrophoresis: Methods and Applications', Universitetsforlaget, Oslo, 1973

Horsch et al, Science 227:1229–1231, 1985

Ibenthal et al, Angew. Bot. 67:97–106, 1993

Jefcoate, Methods in Enzymology 52:258–279, 1978

Kindl et al, Phytochemistry 7:745–756, 1968

Koch et al, 8th Int. Conf. on Cytochrome P450, Abstract PII.053

Koch et al, Archives of Biochemistry and Biophysics, 292:141–150, 1992

König, Z. Angew. Chem. 18:115, 1905

Koziel et al, Biotechnology 11: 194–200, 1993

Lieberei et al, Plant Phys. 90:3–36, 1989

Lüdtke et al, Biochem. Z. 324:433–442, 1953

Lykkesfeldt et al, Plant Physiology 102: 609–613, 1993

Matsuo et al, Phytochemistry 11:697–701, 1972

Murray et al, Nucleic Acids Research 17:477–498, 1989

Nebert et al, DNA Cell Biol. 10:1–14, 1991

Negrutiu et al, Plant Molecular Biology 8:363–373, 1987

Neuhaus et al, Theoretical and Applied Genetics 74:363–373, 1987

Okkels et al, FEBS Letters 237:108–112, 1988

Olin et al, Gene 73: 227–235, 1988

Omura et al, J. Biol. Chem. 239:2370–2378, 1964

Pourmohensi, PhD thesis, Göttingen, 1989

Sambrook et al, Molecular cloning: A laboratory manual. Cold Spring Harbor Laboratory Press, Cold Spring Harbor, N.Y., 1989

Sanger et al, Proc. Natl. Acad. Sci. USA 74:5463–5467, 1977

Schocher et al, Bio/Technology 4:1093–1096, 1986

Shillito et al, Biotechnology 3:1099–1103, 1985

Sibbesen et al, in: 'Biochemistry and Biophysics of cytochrome P-450. Structrue and Function, Biotechnological and Ecological Aspects', Archakov, A. I. (ed.), 1991

Sibbesen et al, 8th Int. Conf. on Cytochrome P450, Abstract PII.016

Underhill, Eur. J. Biochem. 2:61–63, 1967)

Underhill et al, Biochem. Soc. Symp. 38:303–326, 1973

Young et al, Procl. Natl. Acad. Sci USA 82:2583–2587

Wang et, Plant Molecular Biology 11:433–439, 1988

| | | |
|---|---|---|
| EP-240 208-A2 | WO 89/05852 | US 5,023,179 |
| EP-306, 139-A | WO 89/07647 | US 5,231,020 |
| EP 332 104 | WO 91/13992 | |
| EP-452 269-A2 | WO 93/07278 | |
| EP-458 367 A1 | WO 92/09696 | |
| | WO 90/11682 | |

---

What is claimed is:

1. An isolated DNA molecule coding for a cytochrome P-450 monooxygenase that catalyzes the conversion of an amino acid to the corresponding N-hydroxyamino acid and the conversion of said N-hydroxyamino acid to the corresponding oxime.

2. An isolated DNA molecule according to claim 1, wherein said DNA molecule comprises SEQ ID NO: 1.

3. A method of isolating a cDNA molecule coding for a cytochrome P-450 monooxygenase that catalyzes the conversion of an amino acid to the corresponding N-hydroxyamino acid and the conversion of said N-hydroxyamino acid to the corresponding oxime, comprising:

a) isolating and solubilizing microsomes from plant tissue that produces cyanogenic glycosides or glucosinolates;
   b) purifying the cytochrome P-450 monooxygenase;
   c) raising antibodies against the purified cytochrome P-450 monooxygenase;
   d) probing with said antibody a cDNA expression library of plant tissue that produces cyanogenic glycosides or glucosinolates; and
   e) isolating clones that express the cytochrome P-450 monooxygenase.

4. A method of isolating a cDNA molecule coding for a cytochrome P-450 monooxygenase that catalyzes the conversion of an amino acid to the corresponding N-hydroxyamino acid and the conversion of said N-hydroxyamino acid to the corresponding oxime, comprising:

a) isolating and solubilizing microsomes from plant tissue that produces cyanogenic glycosides or glucosinolates;
   b) purifying the cytochrome P-450 monooxygenase;
   c) obtaining a protein sequence of the cytochrome P-450 monooxygenase;
   d) designing oligonucleotides that specify DNA coding for 4 to 15 amino acids of said cytochrome P-450 monooxygenase protein sequence;
   e) probing a cDNA library of plant tissue producing cyanogenic glycosides or glucosinolates with said oligonucleotides, or DNA molecules obtained from PCR amplification of cDNA using said oligonucleotides; and f) isolating clones that encode the cytochrome P-450 monooxygenase.

5. A method for producing a transgenic plant resistant to insects, acarids, or nematodes, comprising:
   a) introducing into a plant cell or plant tissue that can be regenerated into a complete plant, DNA comprising a gene expressible in said plant that encodes a cytochrome P-450 monooxygenase that catalyzes the conversion of an amino acid to the corresponding N-hydroxyamino acid and the conversion of said N-hydroxyamino acid to the corresponding oxime;
   b) selecting transgenic plants; and
   c) identifying transgenic plants that are resistant to insects, acarids, or nematodes.

6. A method for producing a transgenic plant having improved disease resistance or nutritive value, comprising:
   a) introducing into a plant cell or plant tissue that can be regenerated into a complete plant, DNA encoding sense RNA, antisense RNA, or a ribosome, the expression of which reduces the expression of a cytochrome P-450 monooxygenase that catalyzes the conversion of an amino acid to the corresponding N-hydroxyamino acid and the conversion of said N-hydroxyamino acid to the corresponding oxime;
   b) selecting transgenic plants; and
   c) identifying transgenic plants having improved disease resistance or nutritive value.

7. An isolated DNA molecule coding for a cytochrome P-450 monooxygenase that catalyzes the conversion of an oxime to the corresponding nitrile and the conversion of said nitrile to the corresponding cyanohydrine.

8. A method of isolating a cDNA molecule coding for a cytochrome P-450 monooxygenase that catalyzes the conversion of an oxime to the corresponding nitrile and the conversion of said nitrile to the corresponding cyanohydrine, comprising:
   a) isolating and solubilizing microsomes from plant tissue that produces cyanogenic glycosides or glucosinolates;
   b) purifying the cytochrome P-450 monooxygenase;
   c) raising antibodies against the purified cytochrome P-450 monooxygenase;
   d) probing with said antibody a cDNA expression library of plant tissue that produces cyanogenic glycosides or glucosinolates; and
   e) isolating clones that express the cytochrome P-450 monooxygenase.

9. A method of isolating a cDNA molecule coding for a cytochrome P-450 monooxygenase that catalyzes the conversion of an oxime to the corresponding nitrile and the conversion of said nitrile to the corresponding cyanohydrine, comprising:
   a) isolating and solubilizing microsomes from plant tissue that produces cyanogenic glycosides or glucosinolates;
   b) purifying the cytochrome P-450 monooxygenase;
   c) obtaining a protein sequence of the cytochrome P-450 monooxygenase;
   d) designing oligonucleotides that specify DNA coding for 4 to 15 amino acids of said cytochrome P-450 monooxygenase protein sequence;
   e) probing a cDNA library of plant tissue producing cyanogenic glycosides or glucosinolates with said oligonucleotides, or DNA molecules obtained from PCR amplification of cDNA using said oligonucleotides; and
   f) isolating clones that encode the cytochrome P-450 monooxygenase.

10. A method for producing a transgenic plant resistant to insects, acarids, or nematodes, comprising:
    a) introducing into a plant cell or plant tissue that can be regenerated into a complete plant, DNA comprising a gene expressible in said plant that encodes a cytochrome P-450 monooxygenase that catalyzes the conversion of an oxime to the corresponding nitrile and the conversion of said nitrile to the corresponding cyanohydrine;
    b) selecting transgenic plants; and
    c) identifying transgenic plants that are resistant to insects, acarids, or nematodes.

11. A method for producing a transgenic plant having improved disease resistance or nutritive value, comprising:
    a) introducing into a plant cell or plant tissue that can be regenerated into a complete plant, DNA encoding sense RNA, antisense RNA, or a ribosome, the expression of which reduces the expression of a cytochrome P-450 monooxygenase that catalyzes the conversion of an oxime to the corresponding nitrile and the conversion of said nitrile to the corresponding cyanohydrine;
    b) selecting transgenic plants; and
    c) identifying transgenic plants having improved disease resistance or nutritive value.

12. An isolated DNA molecule according to claim 1, wherein said DNA molecule is isolated from a plant that produces cyanogenic glycosides or glucosinolates.

13. An isolated DNA molecule according to claim 1, wherein said DNA molecule is isolated from a plant selected from the group consisting of the genera Sorghum, Trifolium, Linum, Taxus, Triglochin, Mannihot, Amygdalus, Prunus, and cruciferous plants.

14. An isolated DNA molecule according to claim 13, wherein said DNA molecule is isolated from *Sorghum bicolor*.

15. An isolated DNA molecule according to claim 1, wherein said amino acid is selected from the group consisting of tyrosine, phenylalanine, tryptophan, valine, leucine, isoleucine, and cyclopentenylglycine isoleucine.

16. An isolated DNA molecule according to claim 15, wherein said amino acid is tyrosine.

17. An isolated DNA molecule according to claim 1, wherein said cytochrome P-450 monooxygenase has a molecular weight of 57 kD, as determined by SDS-PAGE.

18. An isolated DNA molecule according to claim 1, wherein said cytochrome P-450 monooxygenase comprises an amino acid sequence as shown in SEQ ID NO: 2.

19. An isolated DNA molecule according to claim 1, wherein said cytochrome P-450 monooxygenase comprises an N-terminal amino acid sequence as shown in SEQ ID NO: 3.

20. An isolated DNA molecule according to claim 1, wherein said cytochrome P-450 monooxygenase comprises an internal amino acid sequence selected from the group consisting of SEQ ID NOs: 4–11.

21. An isolated DNA molecule according to claim 20, wherein said cytochrome P-450 monooxygenase comprises an internal amino acid sequence as shown in SEQ ID NO: 4.

22. An isolated DNA molecule according to claim 20, wherein said cytochrome P-450 monooxygenase comprises an internal amino acid sequence as shown in SEQ ID NO: 5.

23. An isolated DNA molecule according to claim 20, wherein said cytochrome P-450 monooxygenase comprises an internal amino acid sequence as shown in SEQ ID NO: 6.

24. An isolated DNA molecule according to claim 20, wherein said cytochrome P-450 monooxygenase comprises an internal amino acid sequence as shown in SEQ ID NO: 7.

25. An isolated DNA molecule according to claim 20, wherein said cytochrome P-450 monooxygenase comprises an internal amino acid sequence as shown in SEQ ID NO: 8.

26. An isolated DNA molecule according to claim 20, wherein said cytochrome P-450 monooxygenase comprises an internal amino acid sequence as shown in SEQ ID NO: 9.

27. An isolated DNA molecule according to claim 20, wherein said cytochrome P-450 monooxygenase comprises an internal amino acid sequence as shown in SEQ ID NO: 10.

28. An isolated DNA molecule according to claim 20, wherein said cytochrome P-450 monooxygenase comprises an internal amino acid sequence as shown in SEQ ID NO: 11.

29. An isolated DNA molecule according to claim 7, wherein said DNA molecule is isolated from a plant that produces cyanogenic glycosides or glucosinolates.

30. An isolated DNA molecule according to claim 7, wherein said DNA molecule is isolated from a plant selected from the group consisting of the genera Sorghum, Trifolium, Linum, Taxus, Triglochin, Mannihot, Amygdalus, Prunus, and cruciferous plants.

31. An isolated DNA molecule according to claim 30, wherein said DNA molecule is isolated from *Sorghum bicolor*.

32. An isolated DNA molecule according to claim 7, wherein said oxime is obtained by the conversion of an amino acid to the corresponding N-hydroxyamino acid and the conversion of said N-hydroxyamino acid to the oxime by another cytochrome P-450 monooxygenase.

33. An isolated DNA molecule according to claim 32, wherein said amino acid is selected from the group consisting of tyrosine, phenylalanine, tryptophan, valine, leucine, isoleucine, and cyclopentenylglycine isoleucine.

34. An isolated DNA molecule according to claim 33, wherein said amino acid is tyrosine.

35. An isolated DNA molecule according to claim 7, wherein the ability of said cytochrome P-450 monooxygenase to convert an oxime to the corresponding nitrile depends on the presence of NADPH and wherein this dependency can be overcome by the addition of reductants.

36. An isolated DNA molecule according to claim 7, wherein said cytochrome P-450 monooxygenase has a molecular weight of 51 kD, as determined by SDS-PAGE.

37. An isolated DNA molecule according to claim 7, wherein said cytochrome P-450 monooxygenase comprises an N-terminal amino acid sequence as shown in SEQ ID NO: 12.

38. An isolated DNA molecule according to claim 7, wherein said cytochrome P-450 monooxygenase comprises an amino acid sequence selected from the group consisting of SEQ ID NOs: 13–16.

39. An isolated DNA molecule according to claim 38, wherein said cytochrome P-450 monooxygenase comprises an amino acid sequence as shown in SEQ ID NO: 13.

40. An isolated DNA molecule according to claim 38, wherein said cytochrome P-450 monooxygenase comprises an amino acid sequence as shown in SEQ ID NO: 14.

41. An isolated DNA molecule according to claim 38, wherein said cytochrome P-450 monooxygenase comprises an amino acid sequence as shown in SEQ ID NO: 15.

42. An isolated DNA molecule according to claim 38, wherein said cytochrome P-450 monooxygenase comprises an amino acid sequence as shown in SEQ ID NO: 16.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
  ( A ) LENGTH: 2143 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i i i ) ANTI-SENSE: NO ( v i ) ORIGINAL SOURCE:
  ( A ) ORGANISM: Sorghum bicolor ( v i i ) IMMEDIATE SOURCE:
  ( B ) CLONE: P-450-Tyr ( x i ) SEQUENCE DESCRIPTION: SEQ ID NO: 1:

| | | | | | | |
|---|---|---|---|---|---|---|
| CCGGCTAGCT | AGCTCATCGG | GTGATCGATC | AGTGAGCTCT | CTCTTTGGCC | TAGCTAGCTG | 60 |
| CTAGCAGTGC | AGGTAGCCAA | TCAAAGCAGA | AGAACTCGAT | CGATCGATCA | TCACGATCGC | 120 |
| TGCTAGCTAG | CTAGCTGCTC | GCTCTCACAC | TAGCTACGTG | TTTTTGTTAA | TTTGATATAT | 180 |
| ATATATAATG | GCGACAATGG | AGGTAGAGGC | CGCGGCCGCC | ACGGTGCTGG | CCGCGCCCTT | 240 |
| GCTGTCCTCC | TCCGCGATCC | TCAAACTGCT | GCTATTCGTA | GTGACGCTCT | CGTACCTGGC | 300 |
| CCGAGCCCTG | AGGCGGCCAC | GCAAAAGCAC | CACCAAGTGC | AGCAGCACAA | CGTGCGCCTC | 360 |
| GCCCCGGCC | GGCGTTGGCA | ACCCGCCGCT | CCCACCGGGT | CCCGTGCCGT | GGCCCGTCGT | 420 |
| CGGCAACCTG | CCGGAGATGC | TGCTGAACAA | GCCGGCATTC | CGCTGGATCC | ACCAGATGAT | 480 |
| GCGCGAGATG | GGCACGGACA | TCGCCTGCGT | CAAGCTTGGC | GGCGTCCACG | TCGTGTCCAT | 540 |
| CACCTGCCCG | GAGATCGCGC | GGGAGGTGCT | CCGGAAGCAG | GACGCCAACT | TCATATCCCG | 600 |
| CCCGCTCACC | TTCGCCTCCG | AGACGTTCAG | CGGCGGGTAC | CGGAACGCCG | TGCTCTCGCC | 660 |
| CTACGGCGAC | CAGTGGAAGA | AGATGCGCCG | CGTCCTCACC | TCCGAGATCA | TCTGCCCGTC | 720 |
| CCGCCACGCC | TGGCTCCACG | ACAAGCGCAC | CGACGAGGCC | GACAACCTCA | CCCGCTACGT | 780 |
| CTACAACCTC | GCCACCAAAG | CCGCCACCGG | CGACGTCGCC | GTCGACGTCA | GGCACGTCGC | 840 |
| TCGTCACTAT | TGCGGCAACG | TTATCCGCCG | CCTCATGTTC | AACAGGCGCT | ACTTCGGCGA | 900 |
| GCCCCAGGCT | GACGGCGGTC | CGGGGCCGAT | GGAGGTGCTG | CATATGGACG | CCGTGTTCAC | 960 |
| CTCCCTCGGC | CTCCTCTACG | CCTTCTGCGT | CTCCGACTAC | CTCCCCTGGC | TGCGGGGCCT | 1020 |
| CGACCTCGAC | GGCCACGAGA | AGATCGTCAA | GGAGGCTAAC | GTGGCGGTGA | ACAGGCTCCA | 1080 |
| CGACACGGTC | ATCGACGACC | GGTGGAGGCA | GTGGAAGAGC | GGCGAGCGGC | AGGAGATGGA | 1140 |
| GGACTTCCTG | GATGTGCTCA | TCACTCTCAA | GGACGCCCAG | GGCAACCCGC | TGCTGACCAT | 1200 |
| CGAGGAGGTC | AAAGCGCAGT | CACAGGACAT | CACGTTCGCG | GCGGTGGACA | ACCCGTCGAA | 1260 |
| CGCCGTGGAG | TGGGCGCTGG | CAGAGATGGT | GAACAACCCG | GAGGTGATGG | CGAAGGCGAT | 1320 |
| GGAGGAGCTG | GACCGCGTCG | TCGGACGGGA | GAGGCTAGTG | CAGGAGTCGG | ACATTCCGAA | 1380 |
| GCTCAACTAC | GTGAAGGCCT | GCATCCGGGA | GGCTTTCCGT | CTGCACCCGG | TGGCGCCCTT | 1440 |
| CAACGTGCCC | CACGTCGCGC | TCGCCGACAC | CACCATCGCC | GGCTACCGCG | TTCCCAAGGG | 1500 |

-continued

| | | | | | |
|---|---|---|---|---|---|
| CAGCCACGTG | ATCCTGAGCC | GCACGGGGCT | GGGCCGCAAC | CCGCGCGTGT | GGGACGAGCC | 1560 |
| CCTGCGCTTC | TACCCGGACC | GACACCTCGC | CACCGCCGCG | TCCGACGTCG | CGCTCACCGA | 1620 |
| GAACGACCTG | CGGTTCATCT | CCTTCAGCAC | CGGCCGCCGC | GGCTGCATCG | CCGCGTCGCT | 1680 |
| CGGCACCGCC | ATGAGCGTCA | TGCTCTTCGG | AAGGCTCCTG | CAGGGGTTCA | CCTGGAGCAA | 1740 |
| GCCCGCCGGG | GTGGAGGCCG | TGGACCTCAG | CGAGTCCAAG | AGCGACACCT | TCATGGCCAC | 1800 |
| CCCGCTGGTG | CTGCACGCTG | AGCCCAGGCT | GCCGGCGCAC | CTCTACCCGT | CCATCTCCAT | 1860 |
| CTGATTAAAC | GTACGGCCGG | TCGTCATTAT | ATTGTATGCA | TATAATTAAA | GACGAGCGAG | 1920 |
| CCTGCTGGTC | ACACTTGCAT | TGCATGTATC | ATCAGCAGGG | GGCTATGCAA | TAAGTTTTTT | 1980 |
| TTTTCCGCGC | TTGATTTCGT | GGTGCTGTGC | GTATTCTGCG | CACACCGACT | GTACGTACGA | 2040 |
| CGGCGTTCAG | CTTTGTATTG | TACCGAGTTA | AAAAGTATTA | TTATTATTAT | CATCGACAAT | 2100 |
| AATAAAAAAA | AAAAAAAAAA | AAAAAAAAAA | AAAAAAAAA | AAA | | 2143 |

( 2 ) INFORMATION FOR SEQ ID NO: 2:

( i ) SEQUENCE CHARACTERISTICS:
        ( A ) LENGTH: 558 amino acids
        ( B ) TYPE: amino acid
        ( D ) TOPOLOGY: linear ( i i ) MOLECULE TYPE: protein ( i i i ) HYPOTHETICAL: NO ( i i i ) ANTI-SENSE: NO ( v i ) ORIGINAL SOURCE:
        ( A ) ORGANISM: Sorghum bicolor ( v i i ) IMMEDIATE SOURCE:
        ( B ) CLONE: P-450-Tyr ( x i ) SEQUENCE DESCRIPTION: SEQ ID NO: 2:

```
Met Ala Thr Met Glu Val Glu Ala Ala Ala Ala Thr Val Leu Ala Ala
 1               5                  10                  15

Pro Leu Leu Ser Ser Ser Ala Ile Leu Lys Leu Leu Leu Phe Val Val
            20                  25                  30

Thr Leu Ser Tyr Leu Ala Arg Ala Leu Arg Arg Pro Arg Lys Ser Thr
        35                  40                  45

Thr Lys Cys Ser Ser Thr Thr Cys Ala Ser Pro Pro Ala Gly Val Gly
    50                  55                  60

Asn Pro Pro Leu Pro Pro Gly Pro Val Pro Trp Pro Val Val Gly Asn
65                  70                  75                  80

Leu Pro Glu Met Leu Leu Asn Lys Pro Ala Phe Arg Trp Ile His Gln
                85                  90                  95

Met Met Arg Glu Met Gly Thr Asp Ile Ala Cys Val Lys Leu Gly Gly
            100                 105                 110

Val His Val Val Ser Ile Thr Cys Pro Glu Ile Ala Arg Glu Val Leu
        115                 120                 125

Arg Lys Gln Asp Ala Asn Phe Ile Ser Arg Pro Leu Thr Phe Ala Ser
    130                 135                 140

Glu Thr Phe Ser Gly Gly Tyr Arg Asn Ala Val Leu Ser Pro Tyr Gly
145                 150                 155                 160

Asp Gln Trp Lys Lys Met Arg Arg Val Leu Thr Ser Glu Ile Ile Cys
                165                 170                 175

Pro Ser Arg His Ala Trp Leu His Asp Lys Arg Thr Asp Glu Ala Asp
            180                 185                 190
```

```
Asn  Leu  Thr  Arg  Tyr  Val  Tyr  Asn  Leu  Ala  Thr  Lys  Ala  Ala  Thr  Gly
          195                     200                      205

Asp  Val  Ala  Val  Asp  Val  Arg  His  Val  Ala  Arg  His  Tyr  Cys  Gly  Asn
     210                      215                      220

Val  Ile  Arg  Arg  Leu  Met  Phe  Asn  Arg  Arg  Tyr  Phe  Gly  Glu  Pro  Gln
225                           230                      235                      240

Ala  Asp  Gly  Gly  Pro  Gly  Pro  Met  Glu  Val  Leu  His  Met  Asp  Ala  Val
                    245                      250                      255

Phe  Thr  Ser  Leu  Gly  Leu  Leu  Tyr  Ala  Phe  Cys  Val  Ser  Asp  Tyr  Leu
               260                      265                      270

Pro  Trp  Leu  Arg  Gly  Leu  Asp  Leu  Asp  Gly  His  Glu  Lys  Ile  Val  Lys
               275                      280                      285

Glu  Ala  Asn  Val  Ala  Val  Asn  Arg  Leu  His  Asp  Thr  Val  Ile  Asp  Asp
     290                      295                      300

Arg  Trp  Arg  Gln  Trp  Lys  Ser  Gly  Glu  Arg  Gln  Glu  Met  Glu  Asp  Phe
305                           310                      315                      320

Leu  Asp  Val  Leu  Ile  Thr  Leu  Lys  Asp  Ala  Gln  Gly  Asn  Pro  Leu  Leu
                    325                      330                      335

Thr  Ile  Glu  Glu  Val  Lys  Ala  Gln  Ser  Gln  Asp  Ile  Thr  Phe  Ala  Ala
               340                      345                      350

Val  Asp  Asn  Pro  Ser  Asn  Ala  Val  Glu  Trp  Ala  Leu  Ala  Glu  Met  Val
               355                      360                      365

Asn  Asn  Pro  Glu  Val  Met  Ala  Lys  Ala  Met  Glu  Glu  Leu  Asp  Arg  Val
     370                      375                      380

Val  Gly  Arg  Glu  Arg  Leu  Val  Gln  Glu  Ser  Asp  Ile  Pro  Lys  Leu  Asn
385                           390                      395                      400

Tyr  Val  Lys  Ala  Cys  Ile  Arg  Glu  Ala  Phe  Arg  Leu  His  Pro  Val  Ala
                    405                      410                      415

Pro  Phe  Asn  Val  Pro  His  Val  Ala  Leu  Ala  Asp  Thr  Thr  Ile  Ala  Gly
                    420                      425                      430

Tyr  Arg  Val  Pro  Lys  Gly  Ser  His  Val  Ile  Leu  Ser  Arg  Thr  Gly  Leu
               435                      440                      445

Gly  Arg  Asn  Pro  Arg  Val  Trp  Asp  Glu  Pro  Leu  Arg  Phe  Tyr  Pro  Asp
     450                      455                      460

Arg  His  Leu  Ala  Thr  Ala  Ala  Ser  Asp  Val  Ala  Leu  Thr  Glu  Asn  Asp
465                           470                      475                      480

Leu  Arg  Phe  Ile  Ser  Phe  Ser  Thr  Gly  Arg  Arg  Gly  Cys  Ile  Ala  Ala
                    485                      490                      495

Ser  Leu  Gly  Thr  Ala  Met  Ser  Val  Met  Leu  Phe  Gly  Arg  Leu  Leu  Gln
               500                      505                      510

Gly  Phe  Thr  Trp  Ser  Lys  Pro  Ala  Gly  Val  Glu  Ala  Val  Asp  Leu  Ser
          515                      520                      525

Glu  Ser  Lys  Ser  Asp  Thr  Phe  Met  Ala  Thr  Pro  Leu  Val  Leu  His  Ala
     530                      535                      540

Glu  Pro  Arg  Leu  Pro  Ala  His  Leu  Tyr  Pro  Ser  Ile  Ser  Ile
545                      550                      555
```

( 2 ) INFORMATION FOR SEQ ID NO: 3:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( i i i ) HYPOTHETICAL: NO (i i i) ANTI-SENSE: NO (v) FRAGMENT TYPE: N-terminal (x i) SEQUENCE DESCRIPTION: SEQ ID NO: 3:

Met Ala Thr Met Glu Val Glu Ala Ala Ala Ala Thr Val Leu Ala Ala
1               5                   10                  15

Pro (2) INFORMATION FOR SEQ ID NO: 4:

(i) SEQUENCE CHARACTERISTICS:
    (A) LENGTH: 7 amino acids
    (B) TYPE: amino acid
    (D) TOPOLOGY: linear (i i) MOLECULE TYPE: protein (i i i) HYPOTHETICAL: NO (i i i) ANTI-SENSE: NO (v) FRAGMENT TYPE: internal (x i) SEQUENCE DESCRIPTION: SEQ ID NO: 4:

Val Trp Asp Glu Pro Leu Arg
1               5

(2) INFORMATION FOR SEQ ID NO: 5:

(i) SEQUENCE CHARACTERISTICS:
    (A) LENGTH: 8 amino acids
    (B) TYPE: amino acid
    (D) TOPOLOGY: linear (i i) MOLECULE TYPE: protein (i i i) HYPOTHETICAL: NO (i i i) ANTI-SENSE: NO (v) FRAGMENT TYPE: internal (x i) SEQUENCE DESCRIPTION: SEQ ID NO: 5:

Tyr Val Tyr Asn Leu Ala Thr Lys
1               5

(2) INFORMATION FOR SEQ ID NO: 6:

(i) SEQUENCE CHARACTERISTICS:
    (A) LENGTH: 16 amino acids
    (B) TYPE: amino acid
    (D) TOPOLOGY: linear (i i) MOLECULE TYPE: protein (i i i) HYPOTHETICAL: NO (i i i) ANTI-SENSE: NO (v) FRAGMENT TYPE: internal (x i) SEQUENCE DESCRIPTION: SEQ ID NO: 6:

Ser Asp Thr Phe Met Ala Thr Pro Leu Val Ser Ser Ala Glu Pro Arg
1               5                   10                  15

(2) INFORMATION FOR SEQ ID NO: 7:

(i) SEQUENCE CHARACTERISTICS:
    (A) LENGTH: 34 amino acids ( B ) TYPE: amino acid
( D ) TOPOLOGY: linear ( i i ) MOLECULE TYPE: protein ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 7:

```
Ala  Gln  Ser  Gln  Asp  Ile  Thr  Phe  Ala  Ala  Val  Asp  Asn  Pro  Ser  Asn
1                   5                        10                       15
Ala  Val  Glu  Xaa  Ala  Leu  Ala  Glu  Met  Val  Asn  Asn  Pro  Glu  Val  Met
                20                      25                       30
Ala  Lys
```

( 2 ) INFORMATION FOR SEQ ID NO: 8:

( i ) SEQUENCE CHARACTERISTICS:
( A ) LENGTH: 13 amino acids
( B ) TYPE: amino acid
( D ) TOPOLOGY: linear ( i i ) MOLECULE TYPE: protein ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 8:

```
Ala  Gln  Gly  Asn  Pro  Leu  Leu  Thr  Ile  Glu  Glu  Val  Lys
1                   5                        10
```

( 2 ) INFORMATION FOR SEQ ID NO: 9:

( i ) SEQUENCE CHARACTERISTICS:
( A ) LENGTH: 9 amino acids
( B ) TYPE: amino acid
( D ) TOPOLOGY: linear ( i i ) MOLECULE TYPE: protein ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 9:

```
Leu  Val  Gln  Glu  Ser  Asp  Ile  Pro  Lys
1                   5
```

( 2 ) INFORMATION FOR SEQ ID NO: 10:

( i ) SEQUENCE CHARACTERISTICS:
( A ) LENGTH: 6 amino acids
( B ) TYPE: amino acid
( D ) TOPOLOGY: linear ( i i ) MOLECULE TYPE: protein ( i i i ) HYPOTHETICAL: NO ( i i i ) ANTI-SENSE: NO ( v ) FRAGMENT TYPE: internal ( x i ) SEQUENCE DESCRIPTION: SEQ ID NO: 10:

```
        Ile  Ser  Phe  Ser  Thr  Gly
        1                  5
```

(2) INFORMATION FOR SEQ ID NO: 11:

(i) SEQUENCE CHARACTERISTICS:
        (A) LENGTH: 12 amino acids
        (B) TYPE: amino acid
        (D) TOPOLOGY: linear (ii) MOLECULE TYPE: protein (iii) HYPOTHETICAL: NO (iii) ANTI-SENSE: NO (v) FRAGMENT TYPE: internal (xi) SEQUENCE DESCRIPTION: SEQ ID NO: 11:

```
        Leu  Pro  Ala  His  Leu  Tyr  Pro  Ser  Ile  Ser  Leu  His
        1                  5                            10
```

(2) INFORMATION FOR SEQ ID NO: 12:

(i) SEQUENCE CHARACTERISTICS:
        (A) LENGTH: 20 amino acids
        (B) TYPE: amino acid
        (D) TOPOLOGY: linear (ii) MOLECULE TYPE: protein (iii) HYPOTHETICAL: NO (iii) ANTI-SENSE: NO (v) FRAGMENT TYPE: N-terminal (xi) SEQUENCE DESCRIPTION: SEQ ID NO: 12:

```
        Met  Asp  Leu  Ala  Asp  Ile  Pro  Lys  Gln  Gln  Arg  Leu  Met  Ala  Gly  Asn
        1                  5                            10                           15
        Ala  Leu  Val  Val
                        20
```

(2) INFORMATION FOR SEQ ID NO: 13:

(i) SEQUENCE CHARACTERISTICS:
        (A) LENGTH: 11 amino acids
        (B) TYPE: amino acid
        (D) TOPOLOGY: linear (ii) MOLECULE TYPE: protein (iii) HYPOTHETICAL: NO (iii) ANTI-SENSE: NO (v) FRAGMENT TYPE: internal (xi) SEQUENCE DESCRIPTION: SEQ ID NO: 13:

```
        Ala  Arg  Leu  Ala  Glu  Ile  Phe  Ala  Thr  Ile  Ile
        1                  5                            10
```

(2) INFORMATION FOR SEQ ID NO: 14:

(i) SEQUENCE CHARACTERISTICS:
        (A) LENGTH: 8 amino acids
        (B) TYPE: amino acid
        (D) TOPOLOGY: linear (ii) MOLECULE TYPE: protein -continued (iii) HYPOTHETICAL: NO (iii) ANTI-SENSE: NO (v) FRAGMENT TYPE: internal (xi) SEQUENCE DESCRIPTION: SEQ ID NO: 14:

Glu Asp Phe Thr Val Thr Thr Lys
1               5

(2) INFORMATION FOR SEQ ID NO: 15:

(i) SEQUENCE CHARACTERISTICS:
   (A) LENGTH: 14 amino acids
   (B) TYPE: amino acid
   (C) STRANDEDNESS: single
   (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 15:

Gln Tyr Ala Ala Leu Gly Ser Val Phe Thr Val Pro Ile Ile
1               5                           10

(2) INFORMATION FOR SEQ ID NO: 16:

(i) SEQUENCE CHARACTERISTICS:
   (A) LENGTH: 6 amino acids
   (B) TYPE: amino acid
   (C) STRANDEDNESS: single
   (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 16:

Xaa Xaa Pro Phe Pro Ile
1               5

(2) INFORMATION FOR SEQ ID NO: 17:

(i) SEQUENCE CHARACTERISTICS:
   (A) LENGTH: 17 base pairs
   (B) TYPE: nucleic acid
   (C) STRANDEDNESS: single
   (D) TOPOLOGY: linear (ii) MOLECULE TYPE: DNA (genomic)

(iii) HYPOTHETICAL: NO (vii) IMMEDIATE SOURCE:
   (B) CLONE: Oligonucleotide specifying AA sequence MEVEAA (xi) SEQUENCE DESCRIPTION: SEQ ID NO: 17:

ATGGARGTNG ARGCNGC                                                                          17

(2) INFORMATION FOR SEQ ID NO: 18:

(i) SEQUENCE CHARACTERISTICS:
   (A) LENGTH: 17 base pairs (B) TYPE: nucleic acid
(C) STRANDEDNESS: single
(D) TOPOLOGY: linear (i i) MOLECULE TYPE: DNA (genomic)

(i i i) HYPOTHETICAL: NO (v i i) IMMEDIATE SOURCE:
(B) CLONE: Oligonucleotide specifying AA sequence DFTMAT (x i) SEQUENCE DESCRIPTION: SEQ ID NO: 18:

GAYACNTTYA TGGCNAC                                                                                               17

(2) INFORMATION FOR SEQ ID NO: 19:

(i) SEQUENCE CHARACTERISTICS:
(A) LENGTH: 42 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (v i i) IMMEDIATE SOURCE:
(B) CLONE: TYROL1b (x i) SEQUENCE DESCRIPTION: SEQ ID NO: 19:

CGGGATCCAT ATGCTGCTGT TATTAGCAGT TTTTCTGTCG TA                                                                    42

(2) INFORMATION FOR SEQ ID NO: 20:

(i) SEQUENCE CHARACTERISTICS:
(A) LENGTH: 33 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (v i i) IMMEDIATE SOURCE:
(B) CLONE: TYROL2

(x i) SEQUENCE DESCRIPTION: SEQ ID NO: 20:

GACCGGCCGA AGCTTTAATT AGATGGAGAT GGA                                                                              33

(2) INFORMATION FOR SEQ ID NO: 21:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (v i i) IMMEDIATE SOURCE:
(B) CLONE: Tyrol3

(x i) SEQUENCE DESCRIPTION: SEQ ID NO: 21:

AGTGGATCCA GCGGAATGCC GGCTT                                                                                       25

(2) INFORMATION FOR SEQ ID NO: 22:

(i) SEQUENCE CHARACTERISTICS:
(A) LENGTH: 17 base pairs ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( v i i ) IMMEDIATE SOURCE:
            ( B ) CLONE: TYROL4

( x i ) SEQUENCE DESCRIPTION: SEQ ID NO: 22:

CGTCATGCTC TTCGGAA                                                                                           1 7

( 2 ) INFORMATION FOR SEQ ID NO: 23:

( i ) SEQUENCE CHARACTERISTICS:
            ( A ) LENGTH: 51 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i i i ) ANTI-SENSE: NO ( v i i ) IMMEDIATE SOURCE:
            ( B ) CLONE: TYROL1d ( x i ) SEQUENCE DESCRIPTION: SEQ ID NO: 23:

CGGGATCCAT ATGGCTCTGT TATTAGCAGT TTTTCTGTCG TACCTGGCCC G                                                     5 1

( 2 ) INFORMATION FOR SEQ ID NO:24:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide with an EcoRI site"

( x i ) SEQUENCE DESCRIPTION: SEQ ID NO:24:

GCAGGAATTC CGG                                                                                               1 3